(12) United States Patent
Kumar

(10) Patent No.: US 8,660,825 B2
(45) Date of Patent: Feb. 25, 2014

(54) METHODS AND SYSTEMS FOR MODELING A PHYSICAL OBJECT

(75) Inventor: Gurunathan Saravana Kumar, Chennai (IN)

(73) Assignee: Indian Institute of Technology Madras, Chennai (IN)

( * ) Notice: Subject to any disclaimer, the term of this patent is extended or adjusted under 35 U.S.C. 154(b) by 0 days.

(21) Appl. No.: 13/564,547

(22) Filed: Aug. 1, 2012

(65) Prior Publication Data

US 2012/0299917 A1    Nov. 29, 2012

Related U.S. Application Data

(63) Continuation of application No. 12/647,072, filed on Dec. 24, 2009, now Pat. No. 8,260,589.

(51) Int. Cl.
*G06F 7/60* (2006.01)
*G06F 17/10* (2006.01)

(52) U.S. Cl.
USPC .......................................................... 703/2

(58) Field of Classification Search
USPC .......................................................... 703/2
See application file for complete search history.

(56) References Cited

U.S. PATENT DOCUMENTS

| | | | |
|---|---|---|---|
| 7,174,282 B2 | 2/2007 | Hollister et al. | |
| 2009/0227161 A1 | 9/2009 | Lambert | |
| 2011/0250688 A1 | 10/2011 | Hasan | |

OTHER PUBLICATIONS

Michel Rieu, "Fractal Fragmentation, Soil Porosity, and Soil Water Properties: I. Theory", 1991, 14 pages.*

Sun, W., et al., 2004. Computer aided tissue engineering: overview, scope and challenges. Biotechnology and Applied Biochemistry, 39(1), 29-47.
Sun, W., et al., 2004. Computer aided tissue engineering: biomimetic modeling and design of tissue scaffold. Biotechnology and Applied Biochemistry, 39(1), 49-58.
Sun, W., Jiang, T. and Lin, F., 2004. A processing algorithm for freeform fabrication of heterogeneous structures. Rapid Prototyping Journal, 10(5), 316-326.
Hutmacher, D.W., 2000. Scaffolds in tissue engineering bone and cartilage. Biomaterials, 21, 2529-2543.
Hollister, S.J., Maddox, R.D. and Taboas, J.M., 2002. Optimal design and fabrication of scaffolds to mimic tissue properties and satisfy biological constraints. Biomaterials, 23, 4095-4103.
Chu, T.M.G., et al., 2002. Mechanical and in vivo performance of hydroxyapatite implants with controlled architectures. Biomaterials, 23, 1283-1293.
Taboas, J.M., et al., 2003. Indirect solid free form fabrication of local and global porous, biomimetic and composite 3D polymer-ceramic scaffolds. Biomaterials, 24, 181-194.

(Continued)

*Primary Examiner* — David Silver
(74) *Attorney, Agent, or Firm* — Foley & Lardner LLP

(57) ABSTRACT

Methods and systems for modeling a porous physical object for layered manufacturing are provided. A model of an object includes geometric and material porosity models, each of which are divided into two-dimensional layer representations. Each two-dimensional layer represents a cross-section of the geometric model and material porosity model of the object, respectfully. The material porosity layer representations specify a material porosity variation for the layer. Geometric and material porosity contours of the model are created by iso-Z surface extraction for each layer. Using the contours, a boundary constrained line representation of each two-dimensional layer representation is generated using continuous space-filling fractal curves to characterize the material porosity variation for each two-dimensional layer.

20 Claims, 18 Drawing Sheets

(56) References Cited

OTHER PUBLICATIONS

Mironov, V., Boland, T., Trusk, T., Forgacs, G. & Markwald, R.R., Organ printing: computeraided jet-based 3D tissue engineering. Trends in Biotechnology 21, 157-61; 2003.

http://en.wikipedia.org/wiki/Tissue_engineering#Synthesis_of_tissue_engineering_scaffolds.

Ma, Peter X.: Scaffolds for tissue fabrication—Materials Today, May 2004, 30-40.

Armillotta, A. and Pelzer, R., 2007. Modeling of porous structures for rapid prototyping of tissue engineering scaffolds. International Journal of Advanced Manufacturing Technology. Available from: http://www.springerlink.com/content/w54841818w317226/.

Masood, S.H., Singh, J.P. and Morsi, Y., 2005. The design and manufacturing of porous scaffolds for tissue engineering using rapid prototyping. International Journal of Advanced Manufacturing Technology, 27, 415-420.

"Design and analysis of tissue engineering scaffolds that mimic soft tissue mechanical anisotropy" Biomaterials, vol. 27, Issue 19, Jul. 2006, pp. 3631-3638.

Biomaterials, vol. 27, Issue 5, Feb. 2006, pp. 735-744.

Ponnusamy Padithevan and Gurunathan Saravana Kumar, "Virtual and Physical Prototyping", Indian Institute of Technology, Guwahati, Dept. of Mechanical Engineering, Sep. 24, 2009, pp. 1-17.

U.S. Non-final Office Action received for U.S. Appl. No. 12/647,072 dated Dec. 19, 2011.

U.S. Notice of Allowance received for U.S. Appl. No. 12/647,072 dated May 11, 2012.

* cited by examiner

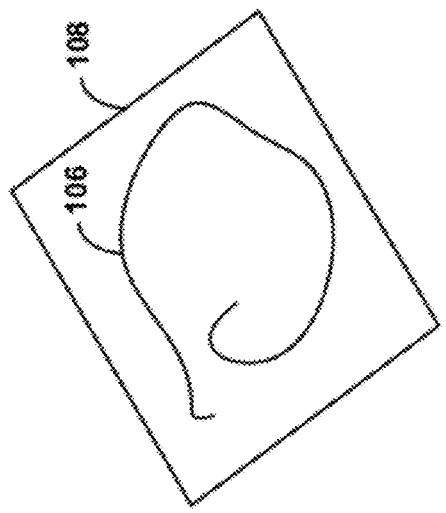
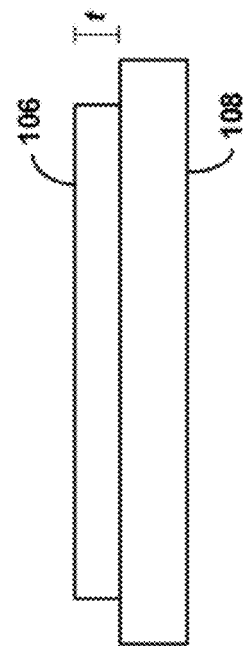
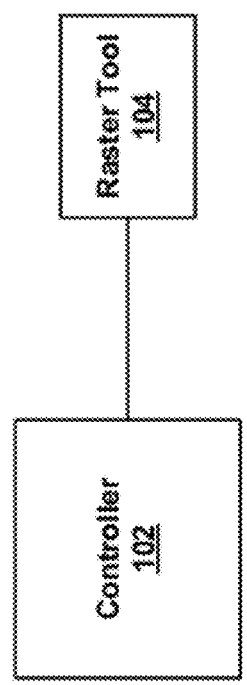
FIGURE 1B
FIGURE 1C
FIGURE 1A

Bezier Cubic Volume

Bezier Cylindrical Volume

Bezier Spherical Volume

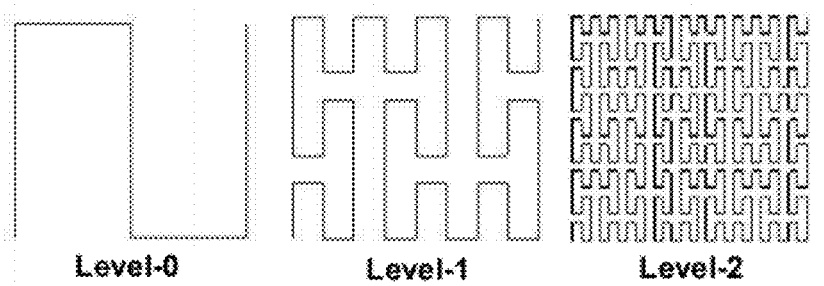
FIGURE 6(a): Peano curve generated up to 3 levels
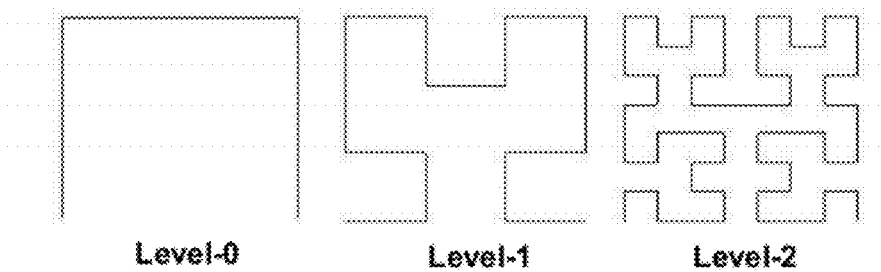
FIGURE 6(b): Hilbert Curve generated up to 3 levels
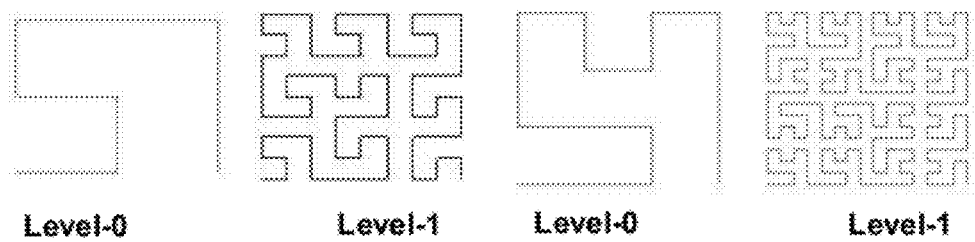
FIGURE 6(c): Macrotile 3x3 and 4x4 curves up to 2 levels
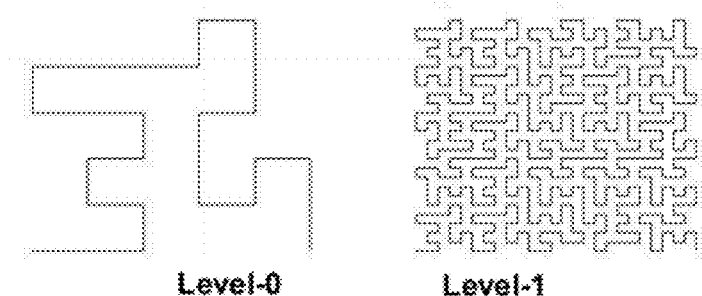
FIGURE 6(d): E-curve curve generated up to 2 levels

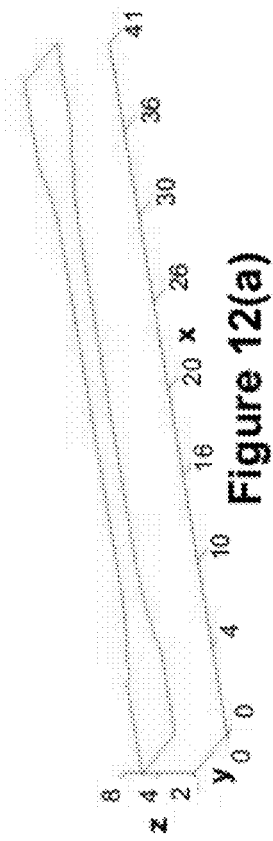
Figure 12(a)
Geometric Slice $GC_i$
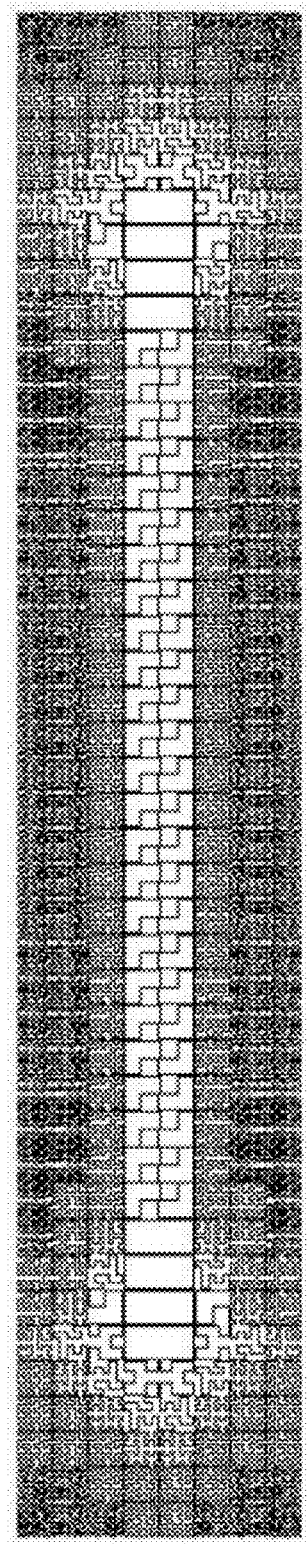
Figure 12(b)
Material Slice $MC_i$
Figure 12(c)
Continuous fractal tool path for the material slice $MC_i$
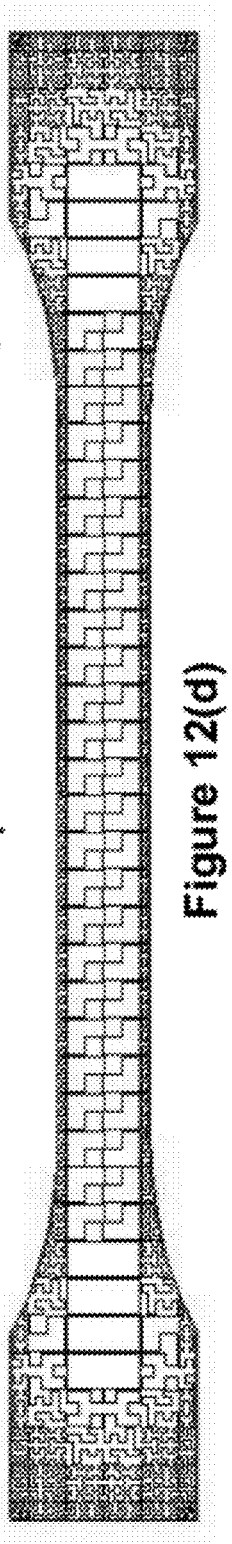
Figure 12(d)
Constrained fractal tool path

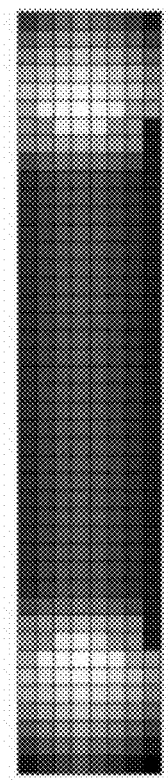
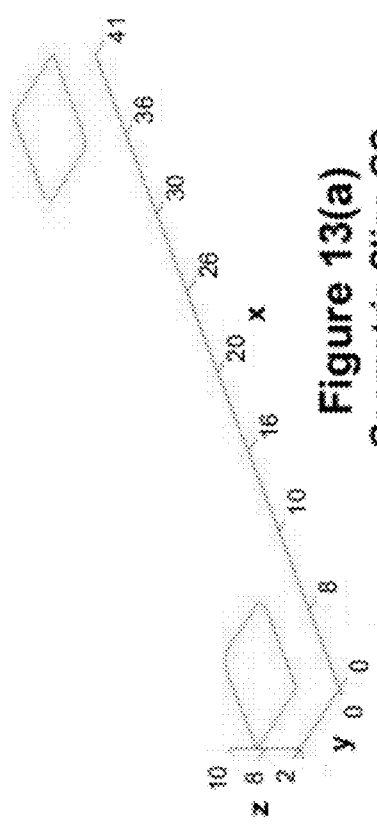
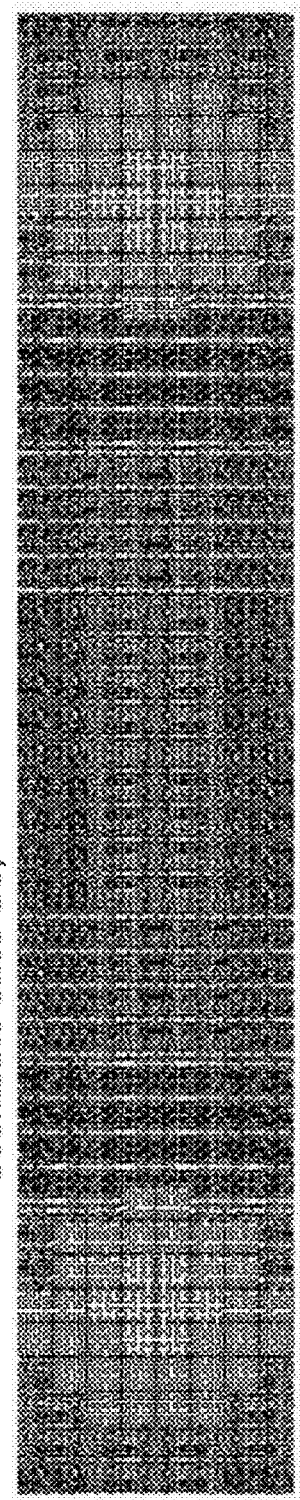
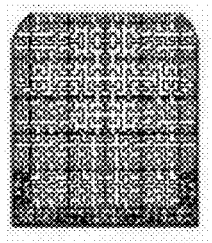
Figure 13(a) Geometric Slice $GC_i$
Figure 13(b) Material Slice $MC_i$
Figure 13(c) Continuous fractal tool path for the material slice $MC_i$
Figure 13(d) Constrained fractal tool path

METHODS AND SYSTEMS FOR MODELING A PHYSICAL OBJECT

CROSS-REFERENCE TO RELATED CASES

The present application is a continuation of U.S. patent application Ser. No. 12/647,072, filed on Dec. 24, 2009, the entire contents of which are herein incorporated by reference.

BACKGROUND

Tissue engineering—an ability to improve or replace biological function through repair or replacement of tissues—enables creation of artificial, fully functional tissues and organs. Expertise from fields such as photo/imprint-lithography (physics), molecular materials (chemistry), process engineering (chemical engineering), simulation and modeling (computer science), mechanical surface modification (mechanical engineering), growth factor control (biochemistry), cell differentiation (cell biology), and more, contribute to viable, scalable industrial solutions.

Success of tissue regeneration depends on an ability to generate reliable, fully integrated, complex, three-dimensional and controlled porous structures called scaffolds of an exact shape and size for a replacement of body parts. Scaffolds are used to enable creation of tissue and/or organ substitutes, for example. Tissue or organ damage, loss, or failure, are frequent and devastating problems faced by the health system (due to trauma, infectious disease, vascular disease, inherited disease, age related disease, congenital anomalies, tumor removal, and complete organ failure, for example), and therefore, several approaches are used to develop viable tissue substitutes for tissue/organ reconstruction, regeneration of damaged tissues and organs, artificial organ/tissue production, and fabrication of living tissue constructs.

Tissue engineering focuses on creating functional tissue using cells seeded onto the three-dimensional (3-D) porous scaffolds. Porous scaffolds provide a 3-D template for cell attachment and growth leading to tissue formation. An internal structure of the scaffold may have channels and interconnected pores in suitable size ranges to help cell attachment, cell proliferation, tissue regeneration, and nutrient flow. An external size and shape of the scaffold may also confirm to a replacement for body part, specific to a subject, for biological and structural acceptability.

Utilization of computer-aided technologies in tissue engineering has enabled integration of advances in biology, biomedical engineering, information technology, and manufacturing technologies. For example, three-dimensional (3-D) printing, fused deposition, stereolithography, selective laser sintering, direct material deposition, or types of layered manufacturing (LM) (also known as rapid prototyping (RP)) are examples of solid free form (SFF) techniques that may be useful for automatic construction of physical objects. In brief, SFF techniques take virtual designs as computer aided design (CAD) models, transform the designs into virtual cross sections, and then enable creation of each cross section in physical space using appropriate materials and processing one after the next until a physical model is completed.

An LM machine may deposit materials in different densities during construction of scaffolds. This can be significant in tissue engineering applications that require material performances to vary with locations in the scaffold, for example, gradients in scaffold pore sizes may be recommended for formation of multiple tissues and tissue interfaces.

SUMMARY

The present application describes example methods and systems for producing three dimensional porous structures with graded porosity and density using solid free form (SFF) techniques, such as but not limited to, 3D printing, fused deposition, stereolithography, selective laser sintering, direct material deposition, or layered manufacturing (LM). For example, the present application describes example frameworks and associated procedures for creating representations of porous geometry for LM. In one example, to vary a volume fraction or porosity of material being deposited in a unit area (and thus to control the porosity), location controlled density raster tool paths are presented using fractal curves. The raster tool path generation uses space-filling fractal curves for LM of porous models.

In one aspect, the present application describes example methods for layered manufacturing (LM) of heterogeneous porous structures using a modeling scheme, a pre-processing algorithm for slicing, and a raster tool path generation based on porosity information. The methods include modeling and data transfer that controls porosity information apart from external geometry of porous objects, for example. The density/porosity data can use space-filling fractal curves at different density patterns as a raster pattern. Space filling fractal curves, such as but not limited to, E-curve, Hilbert, Peano, Macrotile 3×3 and Macrotile 4×4 curves can be used according to the present application.

An example for modeling a physical object includes receiving a model of the object that includes a geometrical model and a material porosity model, and dividing the material porosity model into a series of two-dimensional layer representations. Each two-dimensional layer represents a cross-section of the material porosity model of the object and specifies a material porosity variation for the two-dimensional layer. The method further includes generating a boundary constrained line representation of each two-dimensional layer representation using continuous space-filling fractal curves to characterize the material porosity variation for each two-dimensional layer.

In another aspect, a computer readable medium having stored therein instructions executable by a computing device to cause the computing device to perform functions is provided. The functions include receiving a model of the object that includes a geometrical model and a material porosity model, and dividing the material porosity model into a series of two-dimensional layer representations. Each two-dimensional layer represents a cross-section of the material porosity model of the object and specifies a material porosity variation for the two-dimensional layer. The functions further include generating a boundary constrained line representation of each two-dimensional layer representation using continuous space-filling fractal curves to characterize the material porosity variation for each two-dimensional layer.

In still another aspect, a system is provided that includes a processor, a data storage medium, and machine language instructions stored on the data storage medium and executable by the processor to perform functions. The functions include receiving a model of the object that includes a geometrical model and a material porosity model, and dividing the material porosity model into a series of two-dimensional layer representations. Each two-dimensional layer represents a cross-section of the material porosity model of the object and specifies a material porosity variation for the two-dimensional layer. The functions further include generating a boundary constrained line representation of each two-dimensional layer representation using continuous space-filling fractal curves to characterize the material porosity variation for each two-dimensional layer.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 1 illustrates an example block diagram of a system for creating a physical model.

FIGS. 6(a)-(d) show example space filling fractal curves at different levels of decomposition.

FIGS. 12(a)-(d) illustrate example representations of a slice at height Z=5 cm of the model of FIG. 11.

FIGS. 13(a)-(d) illustrate further example representations of a slice at height Z=8.5 cm of the model of FIG. 11.

DETAILED DESCRIPTION

Figure 2:
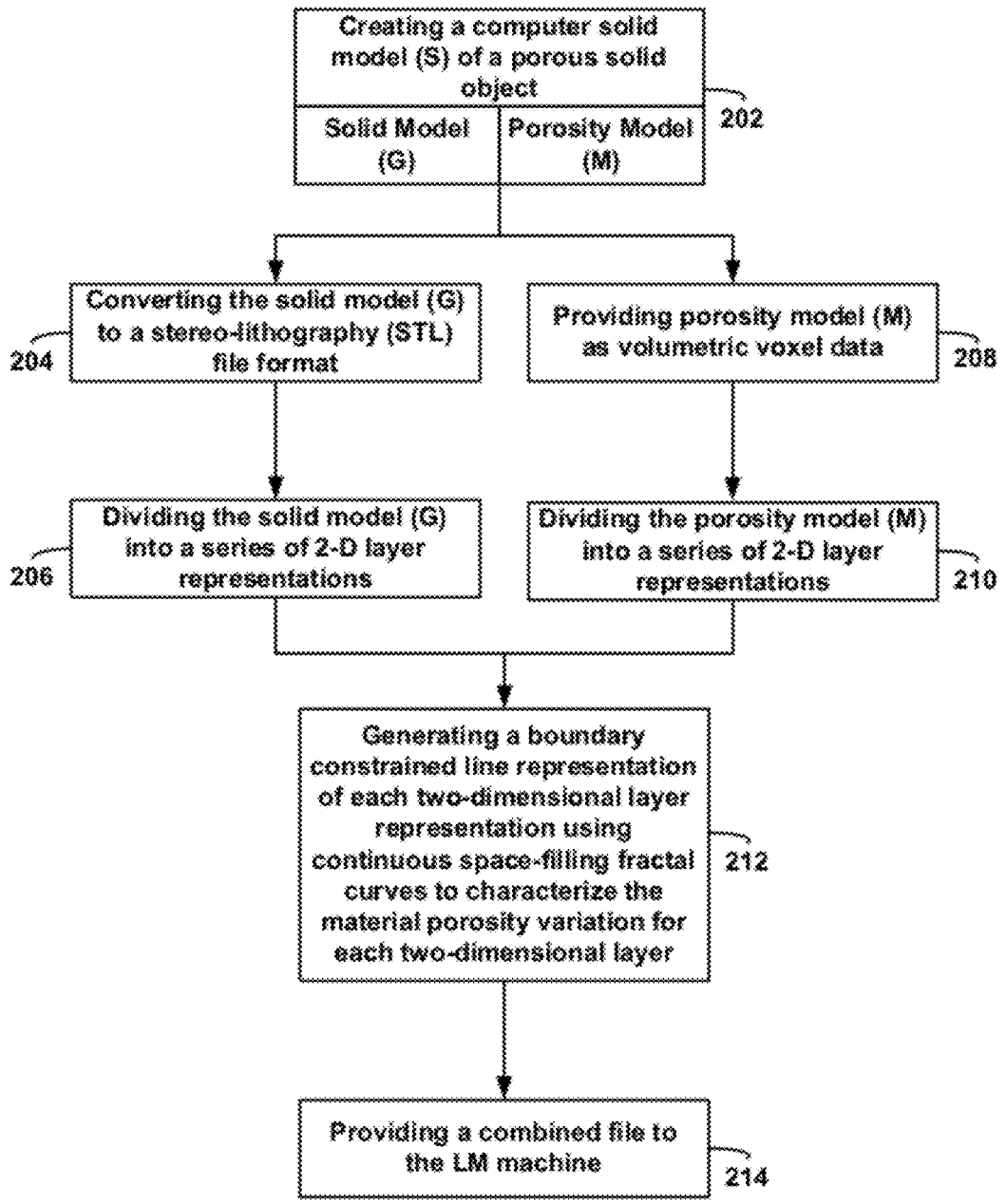
FIG. 2 illustrates an example block diagram of a process for creating a computer solid model used to construct a finished physical model.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and are made part of this disclosure.

In example embodiments below, methods are described for controlling porosity and volume levels of a design of an object. In tissue engineering, for example, to engineer tissue, cells are often implanted into artificial structures that are capable of supporting three-dimensional tissue formation. These structures called scaffolds are used both ex vivo as well as in vivo and influence cells to form into specific microenvironments. Scaffolds can allow cell attachment and migration, deliver and retain cells and biochemical factors, enable diffusion of vital cell nutrients and expressed products, and exert certain mechanical and biological influences to modify behavior of a cell phase, for example.

As an example, scaffolds for tissue engineering are designed to consider a functional requirement, such as but not limited to, an external shape of a replacement, porosity for vessel and nutrient conduit, and factors to stimulate growth of new tissue. To achieve tissue regeneration, scaffolds may include high porosity and an adequate pore size to facilitate cell seeding and diffusion throughout a whole structure of both cells and nutrients, for example. Further, in some embodiments, scaffolds may be required to be biodegradable since the scaffold may be absorbed by surrounding tissues removing a need to surgically remove the scaffold. In addition, if the scaffold is used in an in vitro application, the scaffold may be separated from newly grown tissue, for example. A rate at which degradation of the scaffold occurs may coincide as much as possible with a rate of tissue formation. Example methods for layered manufacturing of controlled porous structure are described herein that can be used for fabricating controlled porous scaffolds for repair and regeneration of tissues.

According to the example methods herein, computer assisted design and manufacturing techniques are used to create scaffolds. As one example, initially, a three-dimensional structure is designed using CAD software, and the scaffold is then realized using ink jet printing of polymer powders or through FDM of a polymer melt. To extend a capability of 3D printing machines for producing graded porous objects, a CAD system with an appropriate modeling scheme to transfer porosity data apart from geometry, slicing, and raster tool path generation (which depends on the porosity information) is presented.

A scaffold model may be defined to include an external geometry and an internal architecture. The external geometry of the scaffold may be designed to have a good fit inside a defect area, for example, or to provide a structure for new tissue growth. Therefore, a shape of the scaffold can be based on clinical computed tomography (CT)/magnetic resonance imaging (MRI) images of the tissue region of interest, and a geometry of the region can be extracted using commercial medical image processing software such as Mimics®, available from Materilise of Ann Arbor, Mich., or Amira® of Germany, for example. A 3-D shape of the tissue region of interest is then exported as a triangulated surface in a stereolithography (STL) file format for physical creation of the object.

The internal architecture of the scaffold can be modeled based on a density and type of tissue to be regenerated. The internal architecture can be modeled as a mathematical volumetric model. The volumetric model of the scaffold can be derived from corresponding clinical images of healthy tissue for a given patient. A set of mathematical correlations based on an image intensity to required porosity can be used for the model as well.

The volumetric model can be an array of 3D voxels (e.g., a volume element representing a value on a regular grid in three dimensional space) with information pertaining to the structure, such as a mechanical modulus and porosity/apparent density. A geometric feature corresponding to a given porosity for a voxel may be modeled at a later stage as suitable tool paths (e.g., deposition paths) while process planning the model for a layered manufacturing technique. This allows processing the information pertaining to the internal architecture in a series of 2-D slices (i.e., layers) rather than in 3-D, and thus, representational and computational complexity can be reduced.

Referring now to the figures, FIG. 1 illustrates a block diagram of a system for creating a physical model. The system generally includes a controller 102 and a raster tool 104. The system may include other components as well. The controller 102 may include a computer, a processor, or a combination of processing means, and the raster tool 104 may include many different types such as a nozzle, a laser beam, etc.

In an LM process, for example, a 3D object is created from a CAD model in a layer-by-layer fashion by depositing a flowable build material through a nozzle carried by a head, and is deposited as a sequence of roads on a base. The build material fuses to previously deposited build material, and solidifies upon a drop in temperature. A position of the head relative to the base is incremented, and the process is repeated to form a 3-D object resembling the CAD model. In the LM process, a layer thickness t of the deposited material, a raster pattern, and a road width of a raster tool path (w) are parameters that control porosity of the deposited volume of material. FIG. 1B illustrates a layer of material 106 deposited onto a base 108 in a raster pattern. The layer of material 106 has a width of the road width of the raster tool (w), and a thickness t, as shown in FIG. 1C.

The volume and porosity of material deposited in a particular slice (i.e., layer) can thus be controlled either by changing (w) or by changing a raster tool path density. The road width (w) depends on the LM system hardware, for example, in the case of FDM, the road width (w) depends on the nozzle size, and in the case of selective laser sintering (SLS), the road width (w) depends on a laser beam diameter. Changing road width (w) dynamically may not be possible in all kinds of LM hardware. According to example methods herein, to vary a volume fraction or porosity of material being deposited in a unit area and thereby to control the porosity, location controlled density raster tool paths are described using fractal curves.

FIG. 2 illustrates a block diagram of a process for creating a computer solid model used to construct a finished physical model. For example, the process of FIG. 2 illustrates an example of a method to create location controlled porous objects by varying the raster tool path pattern and density. Initially, a computer solid model (S) of a porous object is created, as shown at block 202. The solid model (S) contains two types of information: a geometrical model of the object (G) and a material porosity model for the object (M). The process of converting the solid model (S) to a tool path specification for LM hardware is accomplished separately for the geometric model (G) and the material porosity model (M), and information is merged after conversion to provide a tool path.

Information processing for the geometric model (G) involves converting the model to a stereo-lithography (STL) file format, as shown at block 204. Following, the geometric model (G) is sliced/examined to extract contour information from the STL file, as shown at block 206. For example, the 3-D solid model is converted into a series of 2-D layer representations or slices (e.g., contours representing boundaries ($GC_i$=1, 2 ... n)) depending on a slice thickness t specified by a user. Each two-dimensional layer represents a cross-section of the material porosity model of the object and specifies a material porosity variation for the two-dimensional layer. Further, each two-dimensional layer is defined by the contours ($GC_i$=1, 2 ... n) described more fully below.

The material porosity model (M) describing the porosity as a volume fraction for the scaffold can be made available as volumetric voxel data, for example, as shown at block 208. The material porosity model (M) is sliced to yield 2-D layers that are defined by material porosity contours ($MC_i$, i=1, 2 ... n), as shown at block 210, and described more fully below. A slice of the material porosity model specifies a material porosity variation for a corresponding slice from geometry, i.e., for an $i^{th}$ slice, $GC_i$ specifies boundaries and $MC_i$ specifies material porosity variations.

Following a boundary constrained line representation of each two-dimensional layer representation is generated using continuous space-filling fractal curves to characterize the material porosity variation for each two-dimensional layer, as shown at block 212. A tool path for LM includes a boundary contour and raster tool paths (for filling). In example methods, a user can vary the raster tool path density inside the domain as a function of location. For example, for an $i^{th}$ slice, a material porosity contour $MC_i$ specifies the raster path and its density at any given location. The boundaries of the raster tool paths can be defined by the geometric contour $GC_i$. Boundary constrained controlled density raster tool paths are generated from the porosity model M using continuous space filling fractal curves, and the procedure of generating boundary constrained raster tool paths may consider an intersection operator on G and M, which is computationally robust as well as less time expensive since the algorithms work in series of 2D slices rather than 3D solid geometry, for example.

A combined file is then sent to the LM machine, as shown at block 214 to enable creation of a physical object.

Similarly as an example, a material porosity model (M) is created as a background model external to the solid modeling software, and provides material volume fraction information. A domain of the material porosity model (M) is chosen such that the model may completely envelope the geometrical model (G) under consideration. The material porosity model (M) can be constructed with primitive shapes, for example. A choice depends on an object shape and a nature of material porosity gradation required. A final model of an object (S) is the intersection of (G) and (M). Data pertaining to (G) and (M) are separately available in the same co-ordinate system.

To represent background material porosity models (M), Tensor product Bezier solid patches with material porosity as an additional attribute can be used, for example. The Bezier tensor product volume $B^{n,m,l}$ may be defined for a given n, m, l∈N and control points as follows:

$P_{i,j,k} \in E^3$;

i=0, 1, ..., n;
j=0, 1, ..., m;
k=0, 1, ..., l, as, $$B^{n,m,l}(u, v, w) = \sum_{i=0}^{n}\sum_{j=0}^{m}\sum_{k=0}^{l} P_{i,j,k} B_i^n(u) B_j^m(v) B_k^l(w) \in [0, 1] \quad \text{Equation (1)}$$

where n, m, and l are degrees in u, v and w directions respectively and $B_i^n$ is $i^{th}$ Bernstein's polynomial of degree n (e.g., Bernstein's polynomial, $b_{v,n}(x) = \binom{n}{v} x^v (1-x)^{n-v}$, $v = 0, \ldots, n$, and $\binom{n}{v}$ is a binomial coefficient). Control points $P_{ijk}$ of the homogeneous Bezier solid have physical co-ordinates associated with them, i.e., $P_{ijk}(x_{ijk}, y_{ijk}, z_{ijk})$. For representing the material porosity or volume fraction, an additional scalar value ($\rho$) can be added to each control point co-ordinate as $P_{ijk}(x_{ijk}, y_{ijk}, z_{ijk}, \rho_{ijk})$. The material porosity or volume fraction, $\rho$, is represented by a scalar value in the normalized range $0 \leq \rho \leq 1$. According to the material porosity distribution required in a certain region, a user can assign $\rho$ values for control points. The background material porosity model (M) can thus be represented, for example, by tensor product Bezier solid patch as:

$$M \equiv (\rho)^{n,m,l}(u, v, w) \quad \text{Equation (2)}$$
$$= \sum_{i=0}^{n} \sum_{j=0}^{m} \sum_{k=0}^{l} (\rho)_{i,j,k} B_i^n(u) B_j^m(v) B_k^l(w) \in [0, 1]$$

Figure 3A:
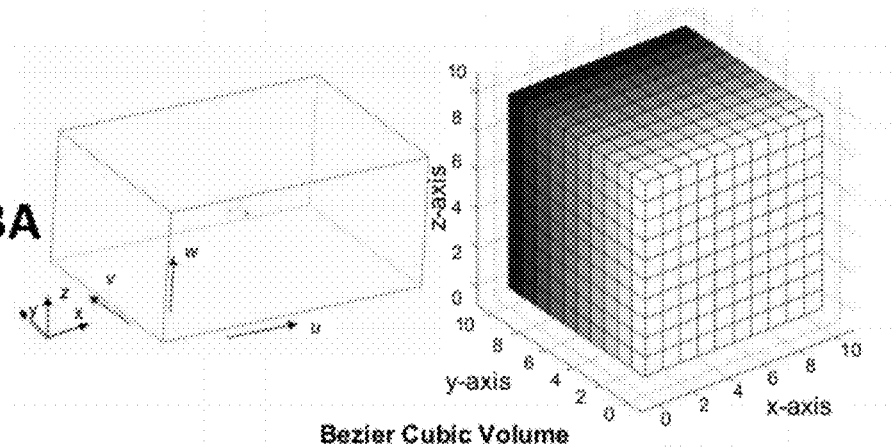
FIGS. 3(a)-(c) show example graphical representations of Bezier volumes with porosity data and their parameterization including volumes for a cube, a cylinder, and a sphere.
Figure 3B:
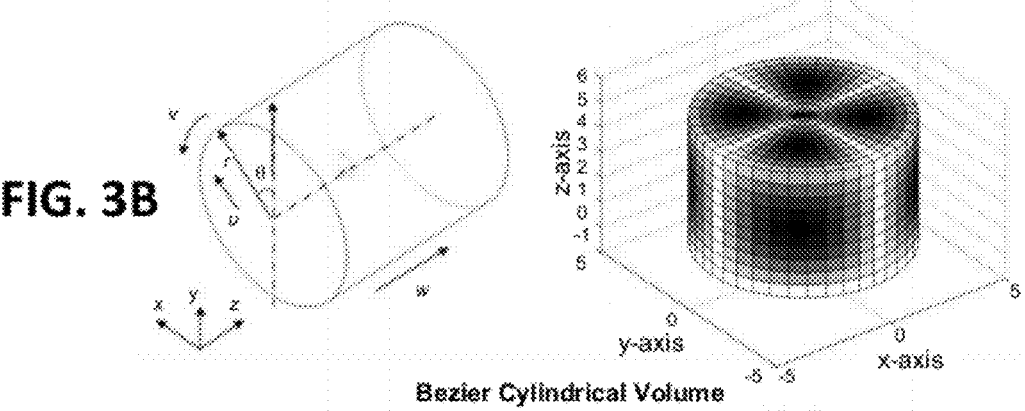
Figure 3C:
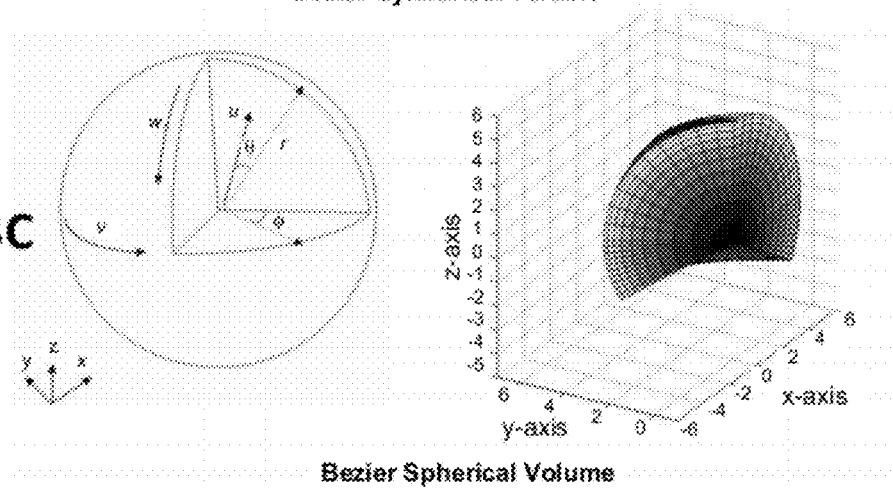

As an example, three types of shapes, namely, cuboid, cylinder and sphere can be used to model (M) and to specify a distribution of material porosity as shown in FIGS. 3(a)-(c). A degree along each parametric direction (e.g., u, v, w as shown in FIGS. 3(a)-(c)) can be modified to provide more freedom in material gradation. Thus, complex gradation (as shown for the cylinder in FIG. 3(b), for example) can be obtained by increasing a degree of the volume, i.e., increasing the control points. As the degree of the tensor product solid patch increases, the rate and direction of gradation (increase/decrease) can be obtained for small parametric increments. Also, a range of parameter values (u, v, w) can be manipulated as shown for the sphere in FIG. 3(c). The gray scale in FIGS. 3(a)-3(c) indicates the volume fraction (p) with dark regions indicating denser material region, for example.

After a geometric model (G) and porosity model (M) are created, the models are divided into layers (i.e., sliced), and a generating tool path is created for each layer and used to form the solid structure. Slicing is the first step in preparing the desired structure by the LM process. The 3-D solid model is converted into a series of 2-D slices (contours representing boundaries) depending on a slice thickness (t) as specified. The slice thickness is specified according to the desired characteristics of the structure. A slice thickness may range from about 0.1 mm to about 1 mm for various commercially available LM technologies.

The solid model (S) comprises the geometric model (G) and the material porosity model (M). The step of slicing is performed separately for the geometric model and the material porosity model. Slicing of the geometrical model (G) is accomplished by a process route where the geometry created in a solid modeling method is converted into an STL file, and then sliced with front end software of the LM system (for example, Insight® in the case of FDM machines from Stratasys®, USA) to provide a series of 2-D contours (GCi, i=1, 2 ... n).

The material porosity model (M) is sliced external to the process route used for geometric model. The slicing of the material porosity model yields 2-D layers that are defined by material porosity contours ($MC_i$, i=1, 2 ... n). A slice of the material porosity model specifies a material porosity variation for the corresponding slice from geometry, i.e., for an $i^{th}$ slice, $GC_i$ specifies the boundaries and $MC_i$ specifies the material porosity variations. The material porosity contours $MC_i$ are generated from the tensor product Bezier volume representation of the model (M) by slicing the evaluated volume at the required Z level. It is possible to control accuracy of evaluation by providing suitable parametric increments, i.e., increments in (u, v, w) for the model (M).

Figure 4A:
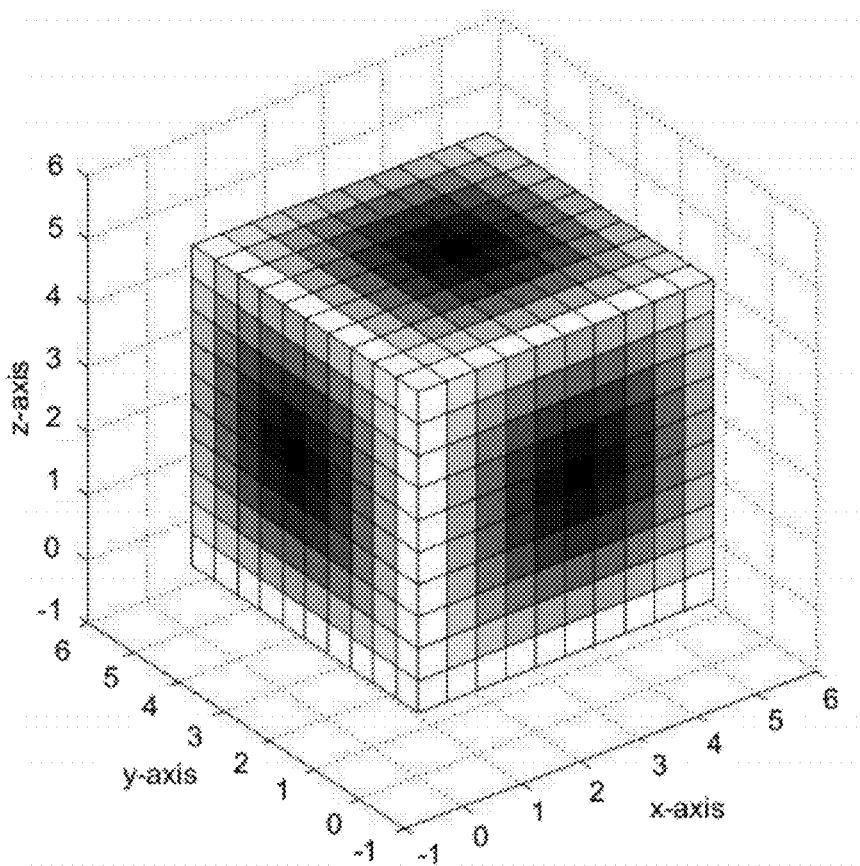
FIG. 4(a) shows an example material porosity model M with cubical shape.
Figure 4B:
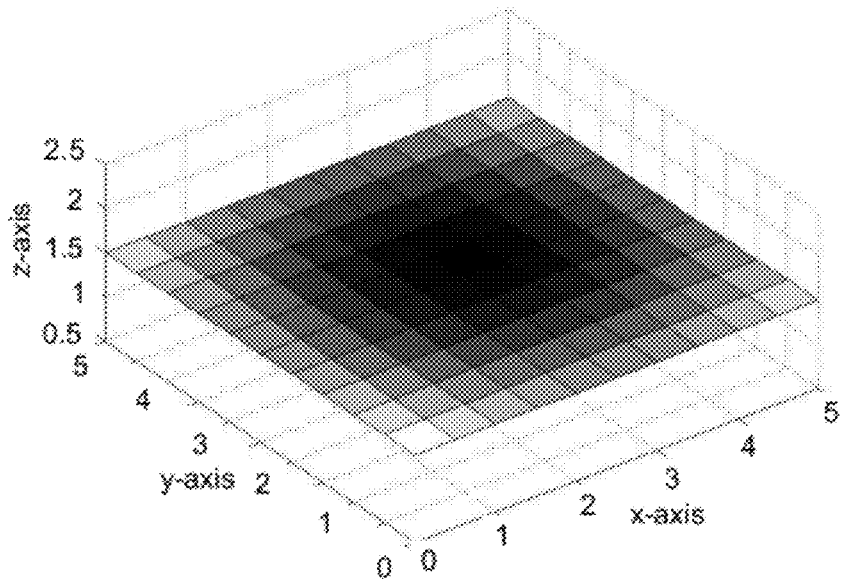
FIG. 4(b) shows an example iso-parametric material surface representing a material porosity contour ($MC_i$).

An example material porosity model (M) with a cuboid shape is shown in FIG. 4(a) and an example slice of the cuboid shape is shown in FIG. 4(b). If one of the parameters, either u, v and w in the case of cuboid and w in the case of a cylinder are aligned along the Z axis (as shown in FIG. 3) the material porosity contour extraction at a given Z value is simplified to extracting an iso-parametric surface of the volume data. In other cases, the iso Z surface may be extracted.

Isosurface extraction generates a surface (or, more generally, a point set) defined by an image of a scalar function of several variables. More specifically, in a three-dimensional array of scalar values (x, y, z) with x=0, ..., xsize-1, y=0, ..., ysize-1, z=0, ..., zsize-1 and an "isovalue" v, eight neighboring data values as vertices of a small cube are referred to as a cell. Each of these cells has an interval [min, max) obtained as a minimum and a maximum of the corresponding eight data values. A visualization of the isosurface includes a list of all cells for which the isovalue v is contained in the interval [min, max).

The tool path for LM is defined by the boundary geometric contours and the material porosity contours. For example, for an $i^{th}$ slice, the material porosity contour $MC_i$ specifies the raster path and its density at any given location. The boundaries of the raster tool paths are defined by the geometric contour $GC_i$. The procedure of generating boundary constrained raster tool paths considers the intersection operator on G and M (described more fully below with respect to FIGS. 8-10).

In example methods, a controlled density raster tool path is generated using continuous space filling fractal curves. Various space filling fractal curves may be used, and each curve follows a different geometric path to fill a given space. A filling area depends on a length of a fractal step d, which in turn, depends on a decomposition level n of the fractal. It can be noted that for all curves, as the decomposition level increases, a density of the continuous curve increases. A density of the curve may be limited by a road width w of the tool (to avoid overlapping, for example). In example embodiments, to obtain a particular volume fraction or material porosity in the scaffold as specified by the porosity contours $MC_i$, an appropriate type of fractal curve and its level of decomposition n for a fixed road width w is chosen, considering the area fraction to be filled and slice thickness t. By changing the fractal curve type and its level for different regions, the desired raster tool path density, and thus the material porosity is obtained in the scaffold.

A fractal is generally a rough or fragmented geometric shape that can be split into parts, each of which is (at least approximately) a reduced-size copy of the whole, a property called self-similarity. Fractal curves can be used for space filling characteristics of a model. Calibration charts provide a choice of fractal curve and its level for a desired material porosity, given a raster path width. Example calibration graphs are provided in FIGS. 7A-7E, described below.

Fractal geometry can be mathematically generated by starting with a pattern that grows through application of a rule set. Fractal curves are continuous, self-similar, non-intersecting space filling curves. Recursive techniques based on well-defined grammar (a set of rules and symbols) are used in generating fractal curves. For example, a turtle graphics' representation or an Lindenmayer system or L-system are formal grammar (a set of rules and symbols) that can be used to generate self-similar fractal curves, for example.

Turtle graphics is a term in computer graphics for a method of programming vector graphics using a relative cursor (the "turtle") upon a Cartesian plane. Seymour Papert created the turtle graphics representation system in 1980 that represents a graphical curve entity by a moving turtle robot and has three attributes: a position, an orientation, and a pen (that has attributes such as color, width, and up versus down).

The turtle moves with commands that are relative to its position, such as "move forward 10 spaces" and "turn left 90 degrees". The pen carried by the turtle can also be controlled, by enabling it, setting its color, or setting its width. The turtle at any given time instant can be represented by a string that contains the above attributes: $\Sigma = \{F, +, -\}$, where F means "draw forward", + means "turn left 90°", and − means "turn right 90°". Considering a starting point of the turtle as (x, y), the turtle can move forward a distance of d in the direction that the turtle is looking (say $\alpha$) from the X-axis. The turtle can also rotate the looking direction anticlockwise or clockwise by an angle $\delta$. Then, the string below in Table 1 can be used as the command to move turtle:

TABLE 1

| | |
|---|---|
| F: | the turtle moves one step forward of length d, in the direction α in which it is looking, the new point (x1, y1) is x1 = x + d * cos(α) and y1 = y + d * cos(α) |
| +: | the turtle rotates through a positive angle, point does not changes but the angle changes to α = α + δ. |
| −: | The turtle rotates through a negative angle, point does not changes but the angle change to α = α − δ. |

L-system grammar can also be used for representation of Fractal curves. L-systems were described by Lindenmayer in 1968. L-system grammars are defined as $L_G = \{V, K, \omega, P\}$, where V (the alphabet) is a set of symbols containing elements that can be replaced (variables), K is a set of symbols containing elements that remain fixed (constants), $\omega$ (start, axiom or initiator) is a string of symbols from V defining the initial state of the system, and P is a set of production rules or productions defining the way variables can be replaced with combinations of constants and other variables.

Figure 5:
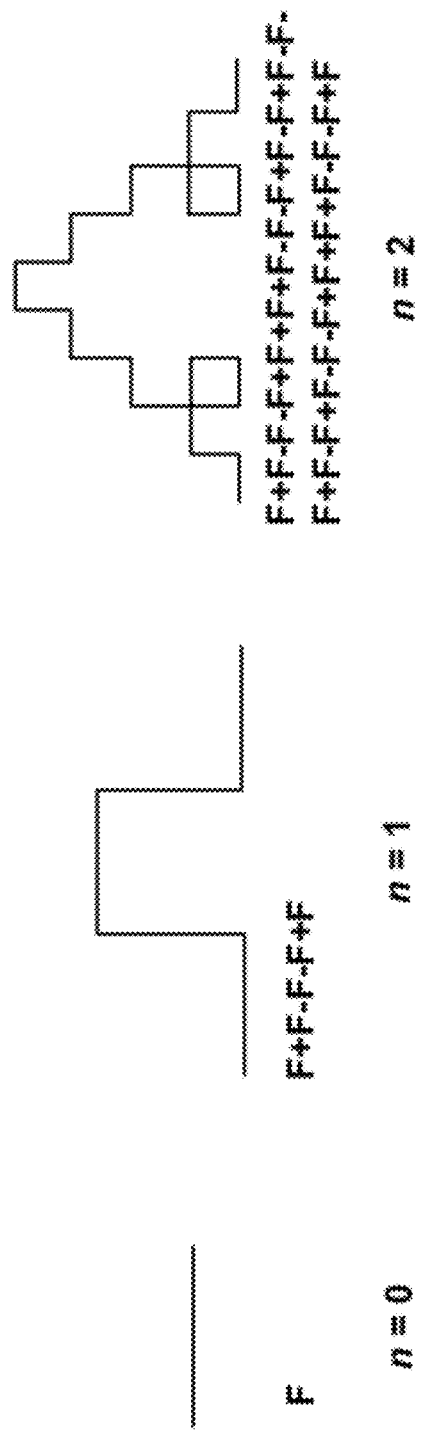
FIG. 5 shows an example of a Koch curve representation in turtle graphics for values of n=0, 1, and 2.

A production system includes two strings; a predecessor and a successor. In this case, as per turtle graphic representation, F means "draw forward", + means "turn left 90°", and − means "turn right 90°". A representative example of generating a variant of the Koch curve is shown in FIG. 5, which uses only right angles to explain a construction of graphical fractal curves using turtle graphics in L-system. Three iterations of generation are shown in the L-system string representation of FIG. 5. The grammar is defined as shown below in Table 2:

TABLE 2

| | |
|---|---|
| variables: | F |
| constants: | +− |
| start: | F |
| rules: | (F → F + F − F − F + F) |
| n = 0: | F |
| n = 1: | F + F − F − F + F |
| n = 2: | F + F − F − F + F + F + F − F − F + F − F + F − F − F + F + F − F − F + F + F − F − F + F |

A space-filling curve is associated with a finite domain in an Euclidean space. In 2-D, the space is bounded by a square and without loss of generality the space intervals [0 1] by [0 1] can be taken.

Space-filling curves in two dimensions are commonly referred to as Peano curves. In an example Peano space-filling fractal curve, the grammar in L-system is as shown below in Table 3:

TABLE 3

| | |
|---|---|
| variables: | L, R |
| constants: | F, +, − |
| start: | L or R |
| rules: | L → LFRFL − F − RFLFR + F + LFRFL |
| | R → RFLFR + F + LFRFL − F − RFLFR |

The Peano curve starts with L or R as a starting string, and a starting point and angle $\delta$ are specified. For each level, terms of L and R are replaced by a corresponding set rule. Finally, only the terms F, +, − are interpreted for the turtle graphics and the terms L and R are erased. Two iterations or levels of decomposition are shown below in Table 4 (equivalent turtle commands are given in brackets):

TABLE 4

| | |
|---|---|
| n = 0: | L (FF − F − FF + F + FF) |
| n = 1: | LFRFL − F − RFLFR + F + LFRFL |
| | (FF − F − FF + F + FF F FF + F + FF − F − FF F FF − F − FF + F + FF etc.) only the first term LFRFL is expanded in terms of turtle command. |

Example illustrations showing this Peano space-filling fractal curve are included in FIG. 6(a). In this case, the angle $\delta$ is 90° with start point (0, 0) in the unit square [0 1], [0 1]. It can be noted that as the level increases, the density of the continuous curve increases. Considering a path represented by the continuous curve as the movement of the turtle (for graphical representation), as the levels increase the distance d moved forward by the turtle for each 'F' command decreases. Mathematically, for the Peano curve, the distance d is related to the level n as follows:

$$d = \frac{0.5}{\left(\sum_{i=1}^{n} 3^{(i-1)}\right)}.$$

Other examples of space filling fractal curves may be used as well, such as the Hilbert curve, the Macrotile 3×3 and Macrotile 4×4 curves, or the E-curve, for example. FIGS. 6(b)-6(d) illustrate examples of such curves. Every curve follows a different geometric path to fill a given space and the filling area depends on a length of a fractal step d, which in turn, depends on a decomposition level n of the fractal.

It can be noted that for the curves shown in FIGS. 6(a)-(d), as the level increases, the density of the continuous curve increases. A percentage area filled, and thus, a porosity can be measured from the geometry. A total length of the fractal curve (l) for a given level n, can be computed by determining a total number of forward commands 'F', say N. An area fraction A (in a unit square) filled by the fractal curve for a road width w is given by:

$$A = N*d*w \qquad \text{Equation (3)}$$

To obtain a particular volume fraction or material porosity as specified by the evaluated material porosity contours $MC_i$, an appropriate type of fractal curve and its level of decomposition n for a fixed road width w are chosen considering the area fraction A and slice thickness t. By changing the fractal curve type and its level for different regions, a desired raster tool path density, and thus, a desired material porosity can be obtained. Fractal curves provide area filling characteristics at various levels of decomposition n and for different road widths w (e.g., 0.02-0.1 cm which covers a range available with different LM processes).

FIGS. 7(a)-7(e) illustrate example graphs and equations of different fractal curves and corresponding levels of decomposition to use for a given road width (w) and a desired material porosity at a location. A number of levels of growth of a fractal curve n and the range of tool path width w for a particular level are considered by a condition that for a given curve type and decomposition level n, a unit step length d for a fractal curve has to be greater than that of the tool path width w, for example.

Figure 7A:
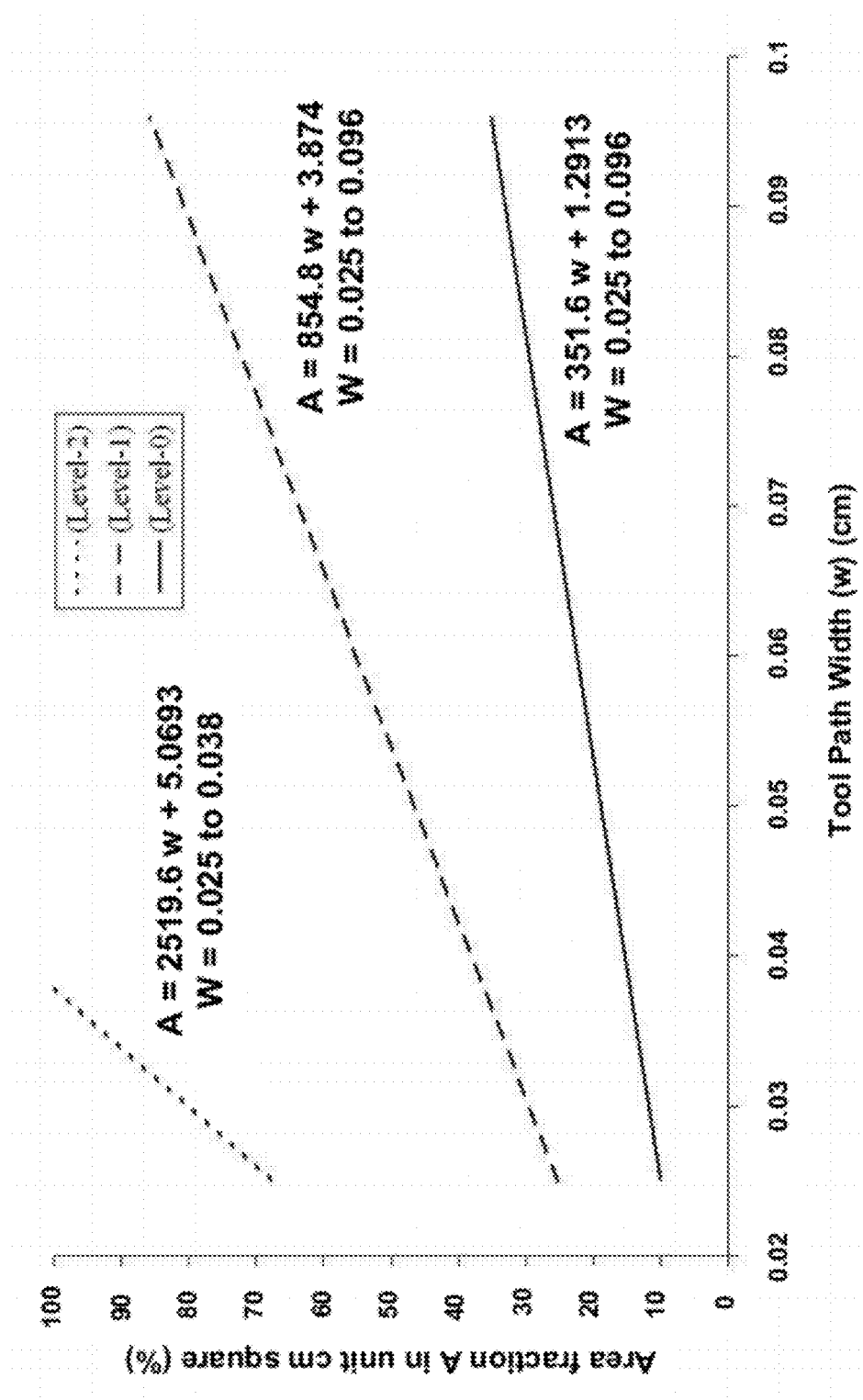
FIG. 7(a) illustrates an example of space filling characteristics of an example Peano curve generated up to 3 levels.

For example, FIG. 7(a) illustrates an example graph of area fraction (A) vs. tool path width (w) for given decomposition levels 0, 1, and 2 of an example of a Peano curve. For a tool path width of about 0.025 cm to about 0.038 cm and an area fraction in the range of about 70%-100%, a level 2 decomposition Peano curve can be used (as shown in FIG. 6(a)). Specific area fraction percentages are determined based on the tool path width (w) according to the equations listed for each decomposition level. For the Peano curve used in FIG. 7(a), the area fractions are determined as shown below in Table 5:

TABLE 5

| | |
|---|---|
| A = 2519.6w + 5.0693, where w = 0.025 to 0.038 | Use Level 2 decomposition |
| A = 854.8w + 3.874, where w = 0.025 to 0.096 | Use Level 1 decomposition |
| A = 351.6w + 1.2913, where w = 0.025 to 0.096 | Use Level 0 decomposition |

Figure 7B:
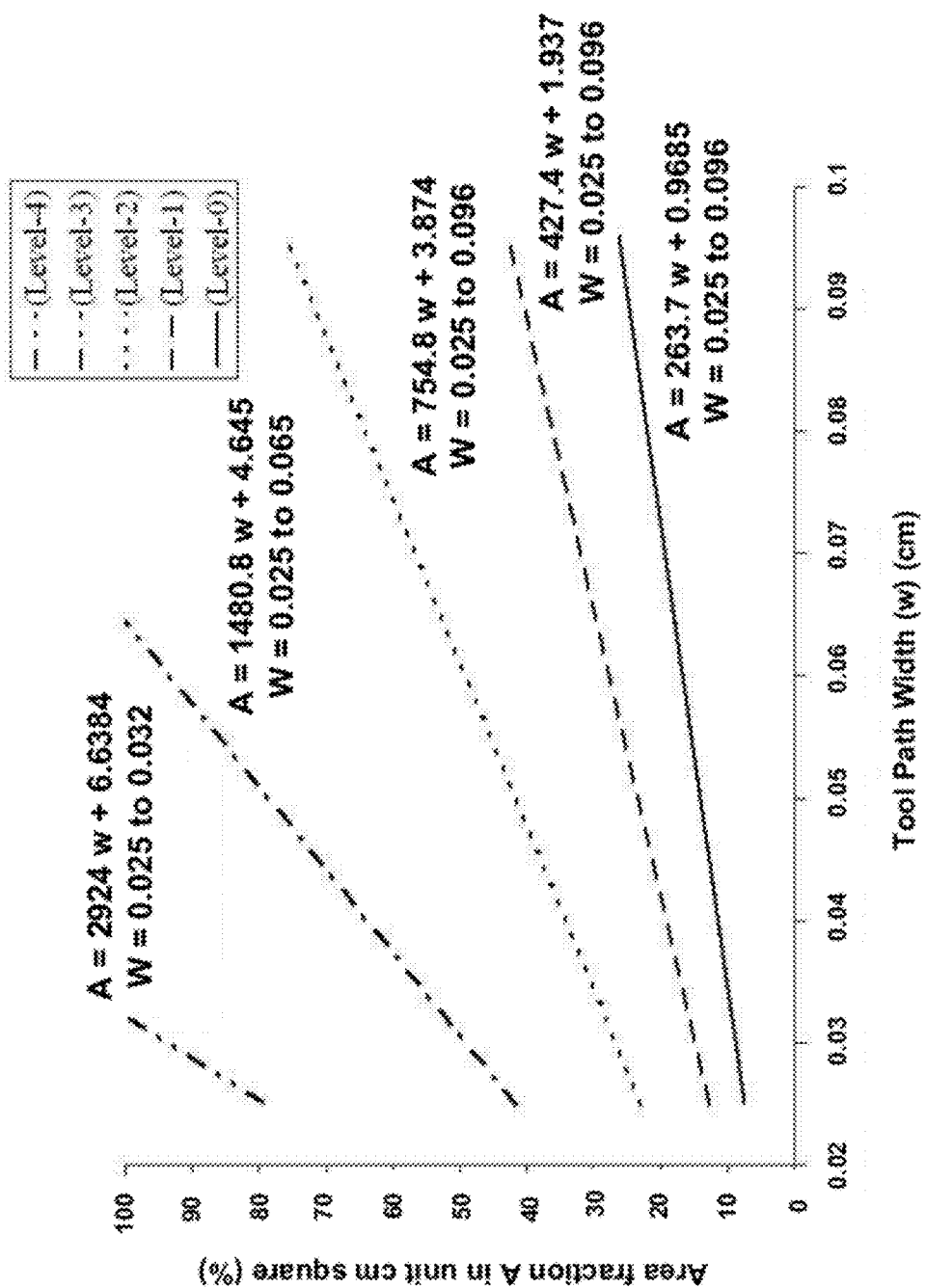
FIG. 7(b) illustrates an example of space filling characteristics of example Hilbert curve generated up to 3 levels.

FIG. 7(b) illustrates a graph and equations for area fraction percentages for different tool paths for a Hilbert fractal curve for decomposition levels 0-4 (as shown in FIG. 6(b)). For the Hilbert fractal curve used in FIG. 7(b), the area fractions are determined as shown below in Table 6:

TABLE 6

| | |
|---|---|
| A = 2924w + 6.6384, where w = 0.025 to 0.032 | Use Level 4 decomposition |
| A = 1480.8w + 4.645, where w = 0.025 to 0.065 | Use Level 3 decomposition |
| A = 754.8w + 3.874, where w = 0.025 to 0.096 | Use Level 2 decomposition |
| A = 427.4w + 1.937, where w = 0.025 to 0.096 | Use Level 1 decomposition |
| A = 263.7w + 0.9685, where w = 0.025 to 0.096 | Use Level 0 decomposition |

Figure 7C:
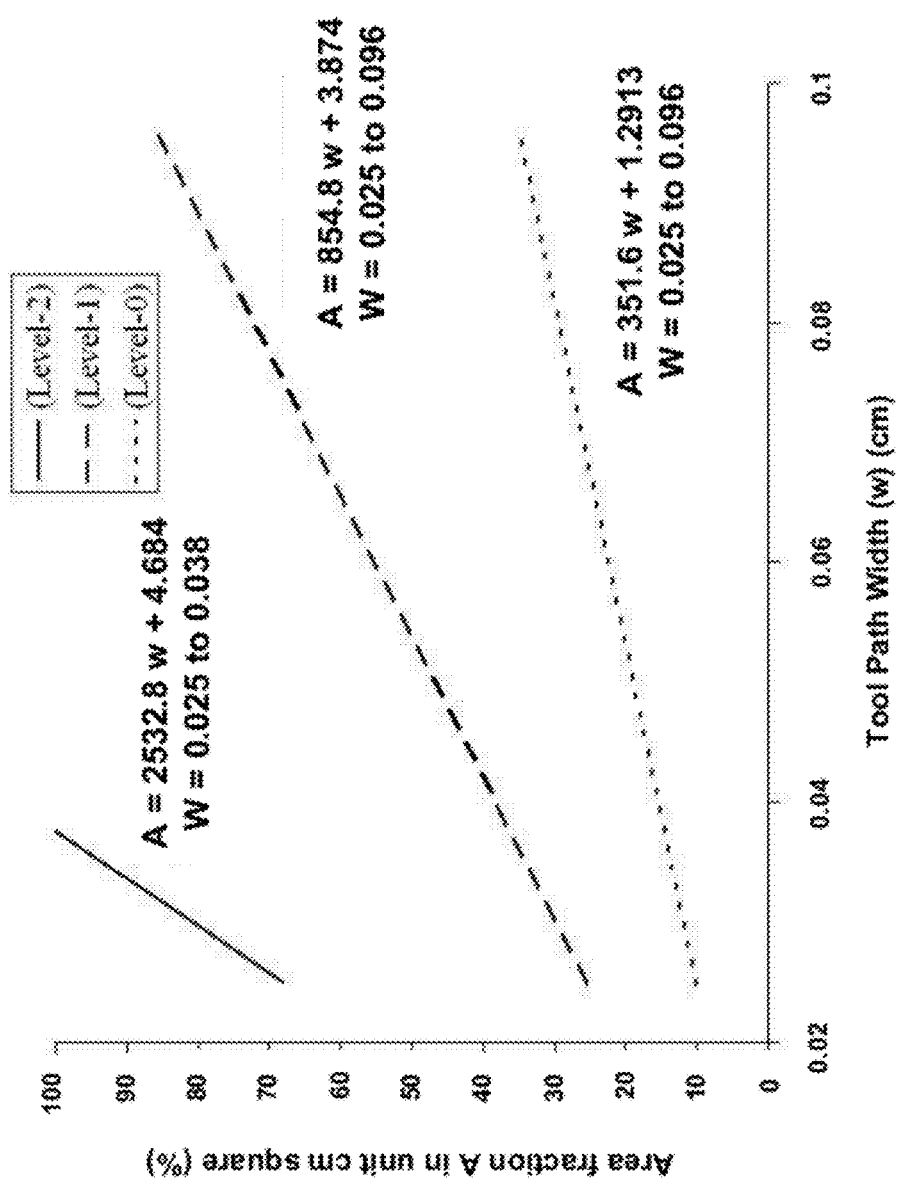
FIG. 7(c) illustrates an example of space filling characteristics of an example Macrotile 3×3 curve generated up to 3 levels.

FIG. 7(c) illustrates a graph and equations for area fraction percentages for different tool paths for a Macrotile 3×3 fractal curve for decomposition levels 0-2 (as shown in FIG. 6(c)). For the Macrotile 3×3 fractal curve used in FIG. 7(c), the area fractions are determined as shown below in Table 7:

TABLE 7

| | |
|---|---|
| A = 2532.8w + 4.684, where w = 0.025 to 0.038 | Use Level 2 decomposition |
| A = 854.8w + 3.874, where w = 0.025 to 0.096 | Use Level 1 decomposition |
| A = 351.6w + 1.2913, where w = 0.025 to 0.096 | Use Level 0 decomposition |

Figure 7D:
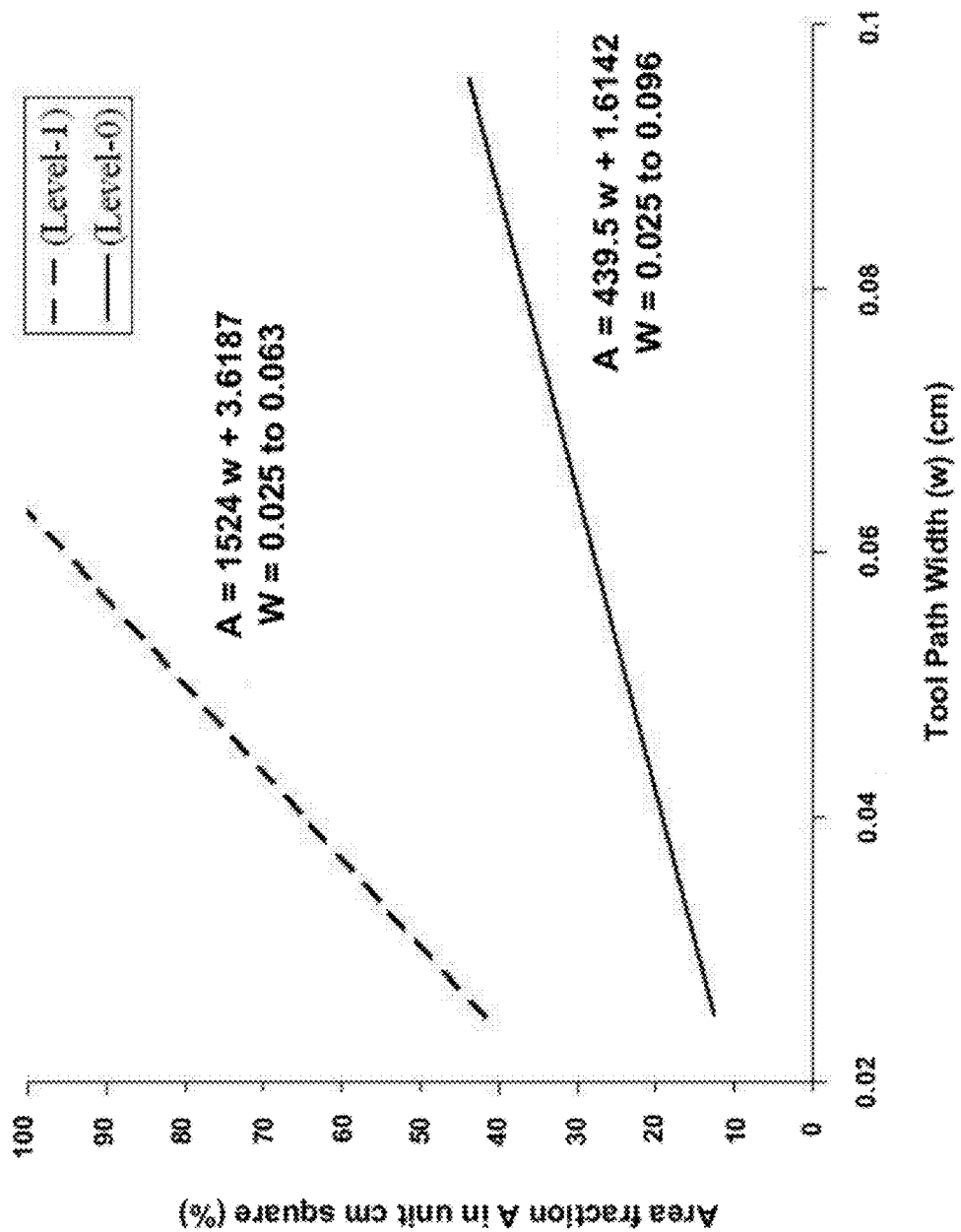
FIG. 7(d) illustrates an example of space filling characteristics of an example Macrotile 4×4 curve generated up to 2 levels.

FIG. 7(d) illustrates a graph and equations for area fraction percentages for different tool paths for a Macrotile 4×4 fractal curve for decomposition levels 0-1 (as shown in FIG. 6(d)). For the Macrotile 4×4 fractal curve used in FIG. 7(d), the area fractions are determined as shown below in Table 8:

TABLE 8

| | |
|---|---|
| A = 1524w + 3.6187, where w = 0.025 to 0.063 | Use Level 1 decomposition |
| A = 439.5w + 1.6142, where w = 0.025 to 0.096 | Use Level 0 decomposition |

Figure 7E:
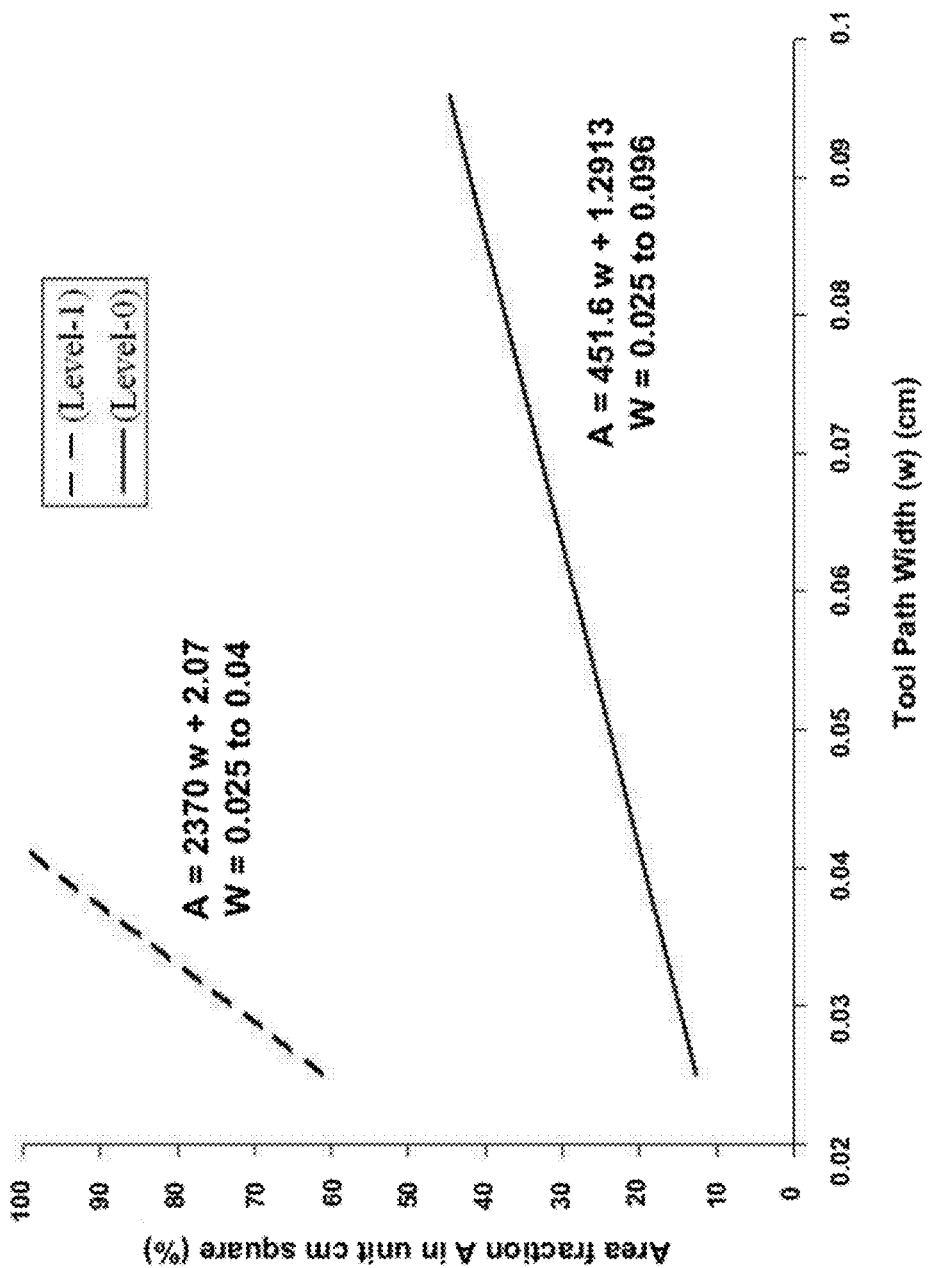
FIG. 7(e) illustrates an example of space filling characteristics of an example E-curve generated up to 2 levels.

FIG. 7(e) illustrates a graph and equations for area fraction percentages for different tool paths for an E-curve for decomposition levels 0-1 (as shown in FIG. 6(e)). For the E-curve used in FIG. 7(e), the area fractions are determined as shown below in Table 9:

TABLE 9

| | |
|---|---|
| A = 1524w + 3.6187, where w = 0.025 to 0.063 | Use Level 1 decomposition |
| A = 439.5w + 1.6142, where w = 0.025 to 0.096 | Use Level 0 decomposition |

Figure 8:
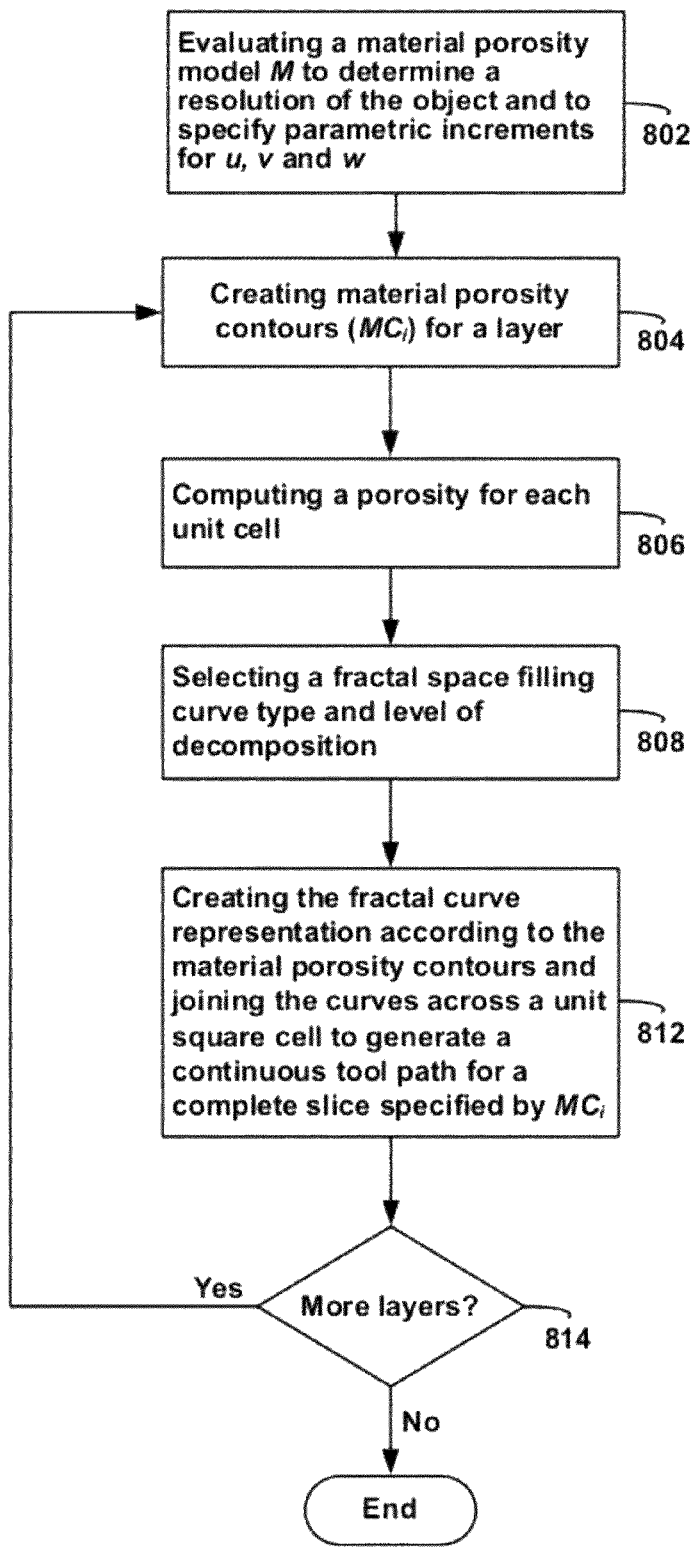
FIG. 8 is a flowchart that depicts example steps of a method for generating boundary constrained raster tool paths.

FIG. 8 is a flowchart that depicts example steps of a method for generating boundary constrained raster tool paths. It should be understood that the flowchart shows functionality and operation of one possible implementation of present embodiments. In this regard, each block may represent a module, a segment, or a portion of program code, which includes one or more instructions executable by a processor for implementing specific logical functions or steps in the process. The program code may be stored on any type of computer readable medium, for example, such as a storage device including a disk or hard drive. In addition, each block may represent circuitry that is wired to perform the specific logical functions in the process. Alternative implementations are included within the scope of the example embodiments of the present application in which functions may be executed out of order from that shown or discussed, including substantially concurrent or in reverse order, depending on the functionality involved, as would be understood by those reasonably skilled in the art.

Initially, as shown at block 802, a material porosity model M is evaluated to determine a resolution of the object, and to specify parametric increments for u, v and w (as illustrated in FIGS. 3(a)-3(c)) to maintain an accuracy of the object. Material porosity contours (MC) are then created by iso-Z surface extraction for the $i^{th}$ slice (e.g., an iso-parametric surface if Z is along a parametric direction), as shown at block 804. The $MC_i$ or evaluated material porosity plane has porosity values for all the rectangular array of nodes (p, u, v if the parameter w is in z direction, for example) as shown in FIG. 3, and can be determined using Equations (1)-(2). The values for the rectangular array are re-sampled to yield porosity data as an array of unit square cells.

A porosity for each cell is then computed as an average of the constituent four nodes (p, u, v, w), and a normalized area fraction A for all the unit square cells in a given slice plane i is computed, as shown at block 806, using Equation (3), for example. A fractal space filling curve type and level of decomposition is then selected based on a road width w (e.g., user input) for each unit square cell in the given slice plane i, as shown at block 808. Tables 5-9 above illustrate example equations for selecting fractal curve types for a given area fraction.

Figure 9:
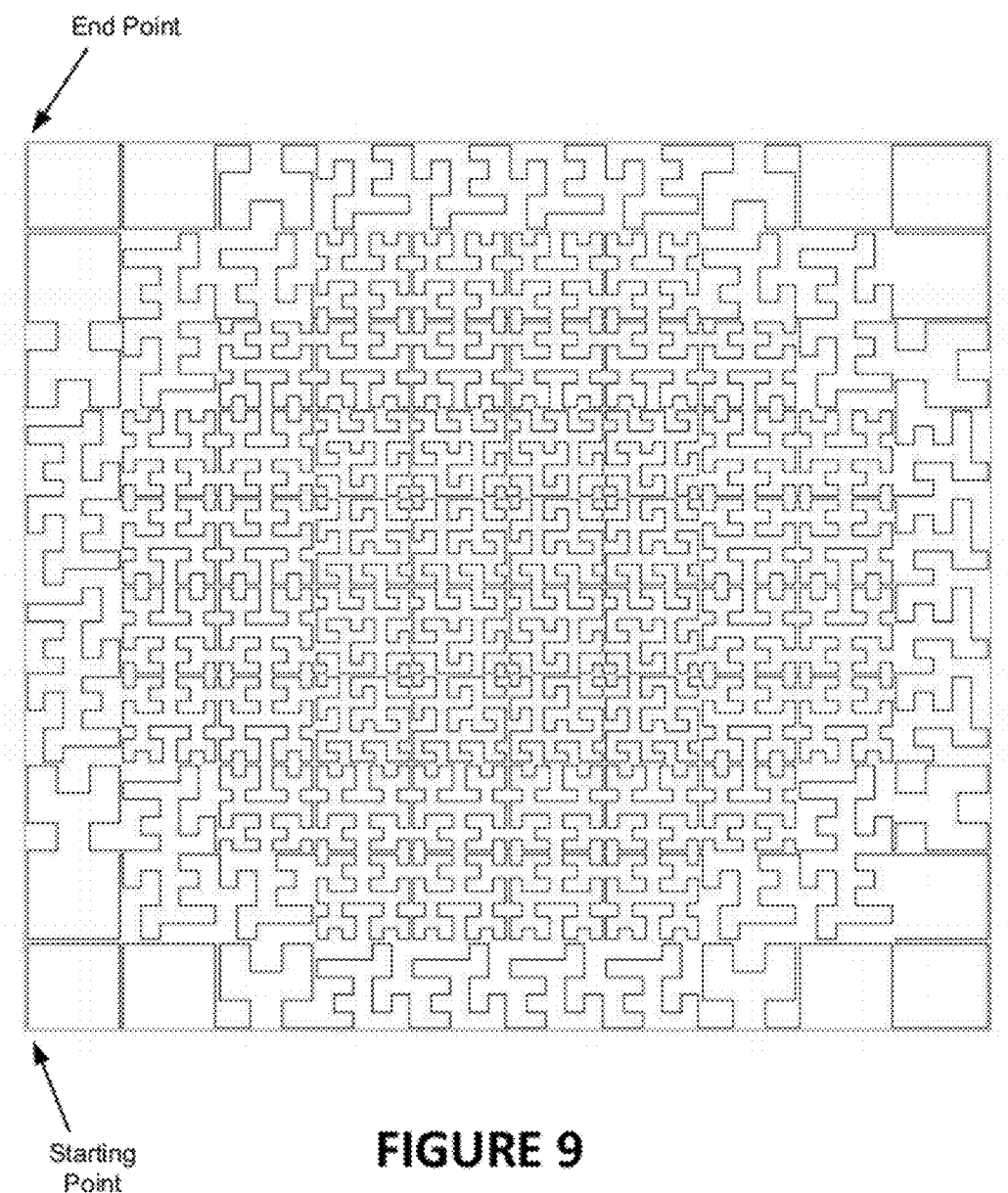
FIG. 9 is an example illustration of generation of a continuous tool path by joining different fractal curves at different levels to represent a material porosity variation specified by $MC_i$ for a general slice i.

Fractal curves are then drawn according to the material porosity contours and joined across a unit square cell to generate a continuous tool path for a complete slice specified by $MC_i$, as shown at block 810. For example, for an arbitrary general material porosity variation specified by $MC_i$ for a slice i, resulting fractal curves for each unit cell may be of a different type and/or at different levels so as to obtain a required filled area fraction. Two adjacent unit cells (in tool travel direction) in a general material distribution should have start and end points of the corresponding fractal curve located so as to join the start and end points without any additional or redundant tool travel. This can be accomplished by first adding tool path turning operators (+) or (−), i.e., to turn 90° left or right, as required at an end of a tool path in a unit cell. Secondly, appropriate start point and direction of the fractal curve for the adjacent cell is selected. The overall tool travel may be from left to right in a row of cells, and in a row immediately above it is from right to left. FIG. 9 is an example illustration of generation of a continuous tool path by joining different fractal curves at different levels to represent a material porosity variation specified by $MC_i$ for a general slice i. Each unit square in FIG. 9 includes a fractal curve of a specific level. Unit squares located at a boundary of FIG. 9 include fractal curves of a low level, while the unit squares at a center of FIG. 9 include fractal curves of a higher level to represent a more dense (less porous) area, for example.

Figure 10:
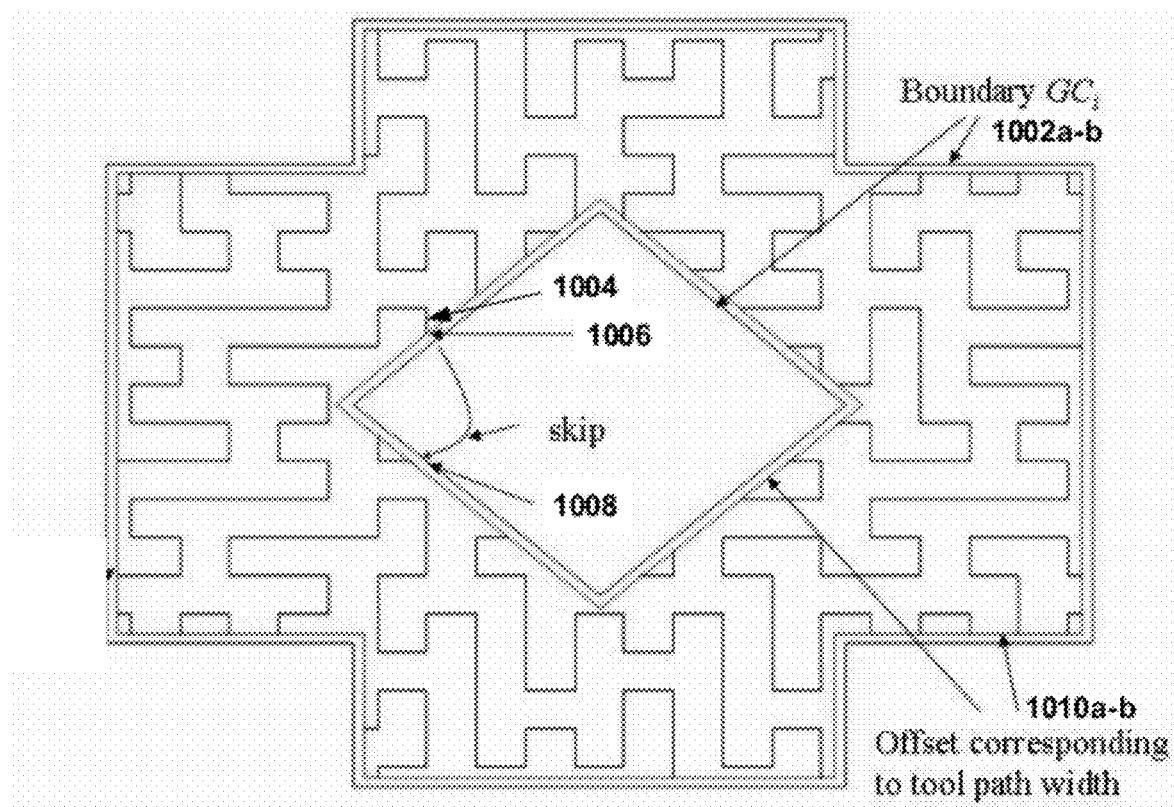
FIG. 10 illustrates an example of a layer of an object with internal and external boundaries.

Referring back to the method of FIG. 8, after joining the fractal curves of all unit squares, the fractal curves are then trimmed based on boundary data from $GC_i$, as shown at block 812. Boundary data $GC_i$ for an arbitrary general object includes contours in a series of edge loops as depicted, for example, in FIG. 10. The edge loops are non-self intersecting and traverse in anti-clockwise and clockwise directions, respectively, for external and internal boundaries. This example convention is from a boundary representation data structure such that a material region is on a left side of the boundary as per the traversal direction. An edge loop includes edges and vertices that are connected to give an overall topological relation. In a slice data (generated from STL files) the edge is a line segment. A continuous tool path including fractal curves is trimmed according to boundary data in $GC_i$. Trimming can be accomplished by finding points of intersection of the continuous fractal tool path with a boundary. The intersection points are ordered serially in the order of their occurrence from the start to the end point of the continuous fractal path. The start point of the fractal path is defined to be outside the external boundary represented by $GC_i$ because the material contour $MC_i$ envelops a given $GC_i$ for any slice plane i. Thus, the first intersection point occurring along the fractal tool path implies that the path is entering the material region, and a next intersection point implies that the path is entering a void region. In this manner, all intersection points are flagged as 'in' and 'out' to signify that the path is entering or leaving the material region. In terms of the LM process, for example, this signifies whether the nozzle or laser should be 'on' or 'off' respectively. The path between 'off' and 'on' areas can be skipped by the controller to minimize a time of traversal. FIG. 10 illustrates a layer of an object with internal and external boundaries 1002a-b. A center of the layer is hollow. Thus, when drawing a fractal curve line segment, such as segment 1004, the segment 1004 is defined to be off while the tool traverses between boundary points 1006 and 1008 so as to skip the non-material region. The line segment 1004 is then defined to be on once the tool traverses past boundary point 1008, for example. Thus, because the fractal tool path and the boundary data are available as line segments, intersection or trimming can be accomplished using a line to line intersection technique as described.

The fractal curve representation shown in FIG. 10 includes an offset distance between an edge fractal curve and a boundary. For example, offsets 1010a-b are included between the boundary and edges of fractal curves that is approximately equal to a length of the tool path width. This offset takes care of the tool path width compensation for boundary curves so that the external geometry is accurate and also avoids material overlap during material deposition, for example.

Referring back to the method of FIG. 8, the steps 804-812 are repeated for all slices i=1, 2 . . . n to generate a representation of the solid object, as shown at block 814.

Figure 11:
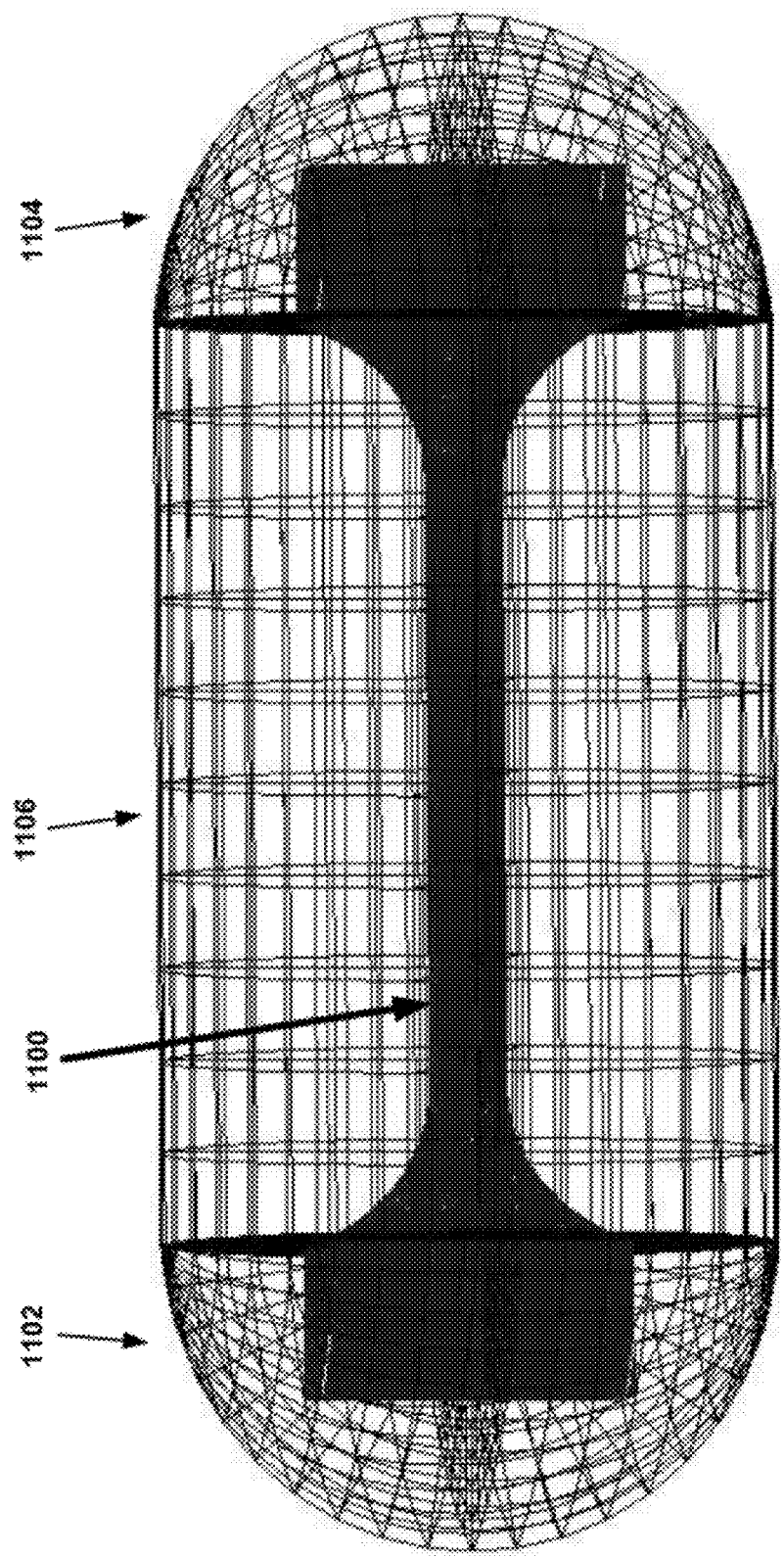
FIG. 11 illustrates an example geometric model G including a tensile test specimen.

Using example methods described herein, a tool path is created for manufacturing a porous object in an LM system, for example. As one example, a geometric model G may be a tensile test specimen 1100 modeled in a computer program (e.g., using ProE software) and an illustration of an example of the modeled object from a corresponding STL file is shown in FIG. 11. Size limits of the modeled objects are 40 cm, 5 cm, and 10 cm along X, Y and Z axes, respectively. The material model M can be created using a computer program product, such as Matlab. For example, a mathematical model of the object 1100 is created using a combination of three Bezier material primitives, two of which may be half-hemispheres 1102 and 1104 corresponding to the specimen ends, and a third as a cylinder 1106 corresponding to the specimen shaft as shown in FIG. 11. A shape, size, and location of the primitive shapes are chosen according to the geometry of the specimen. In the present example, a porosity model is chosen such that a porosity decreases from a center toward a boundary. The models G and M constitute the solid model S for the tensile test specimen model. The models G and M are then divided into two dimensional slices.

Slices of geometric model, $GC_i$, are generated using STL slicing software and the slices for material model, $MC_i$ are generated as well (as described herein). A representative slice at height Z=5 is shown in FIG. 12. For example, a geometric slice representation is shown in FIG. 12(a), and a material slice representation is shown in FIG. 12(b). Using calibration charts and equations described above, appropriate combinations of fractal space filling curves were selected and combined to generate a fractal tool path for a tool path width w=0.05 cm. FIG. 12(c) illustrates the continuous fractal tool path for a material slice $MC_i$. A boundary constrained tool path for the representative slice is also shown in FIG. 12(d).

A second representative slice at height 8.5 cm is shown in FIG. 13 in which FIG. 13(a) illustrates a geometric slice representation of the slice, FIG. 13(b) illustrates a material slice representation of the slice, FIG. 13(c) illustrates the continuous fractal tool path for a material slice $MC_i$, and FIG. 13(d) illustrates a boundary constrained tool path for the representative slice.

In embodiments described herein, example raster path generation methods use space-filling fractal curves to enable heterogeneous modeling of porous objects, and integration to LM for realizing physical prototypes. The example methods enable modeling and data transfer that includes modeling controlled porosity information apart from external geometry of porous objects.

LM technology also enables use of multiple materials in different compositions in the construction of objects. Thus, in certain applications, materials performance may vary with locations within the component. One such example is tissue engineering, particularly for replacement or repair of damaged tissues. Every tissue has a unique architecture that includes mainly a cellular component and a scaffold. In developing tissue substitutes, providing a scaffold (an alternative to natural support component) and control over structure porosity in such scaffolds may be desired. For example, scaffold porosity and internal pore architecture parameters, such as but not limited to, pore geometry, size, interconnectivity, orientation, and branching are linked to nutrient diffusion, interstitial fluid and blood flow, controlling cell growth and function, manipulating tissue differentiation, and improving scaffold physical function and regenerated tissue physical properties.

Figure 14:
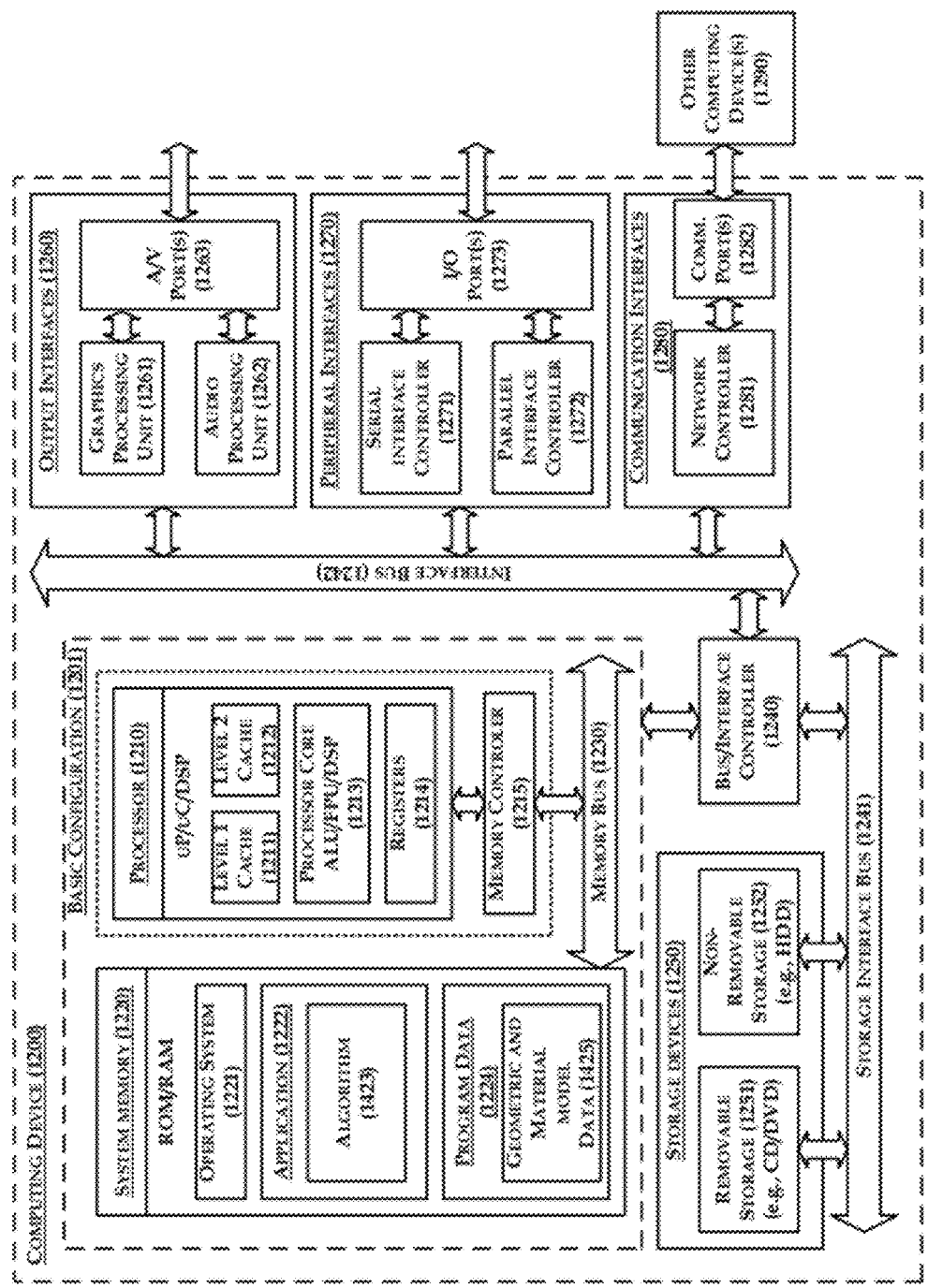
FIG. 14 is a block diagram illustrating an example computing device arranged for generating a raster tool path.
Figure 14:
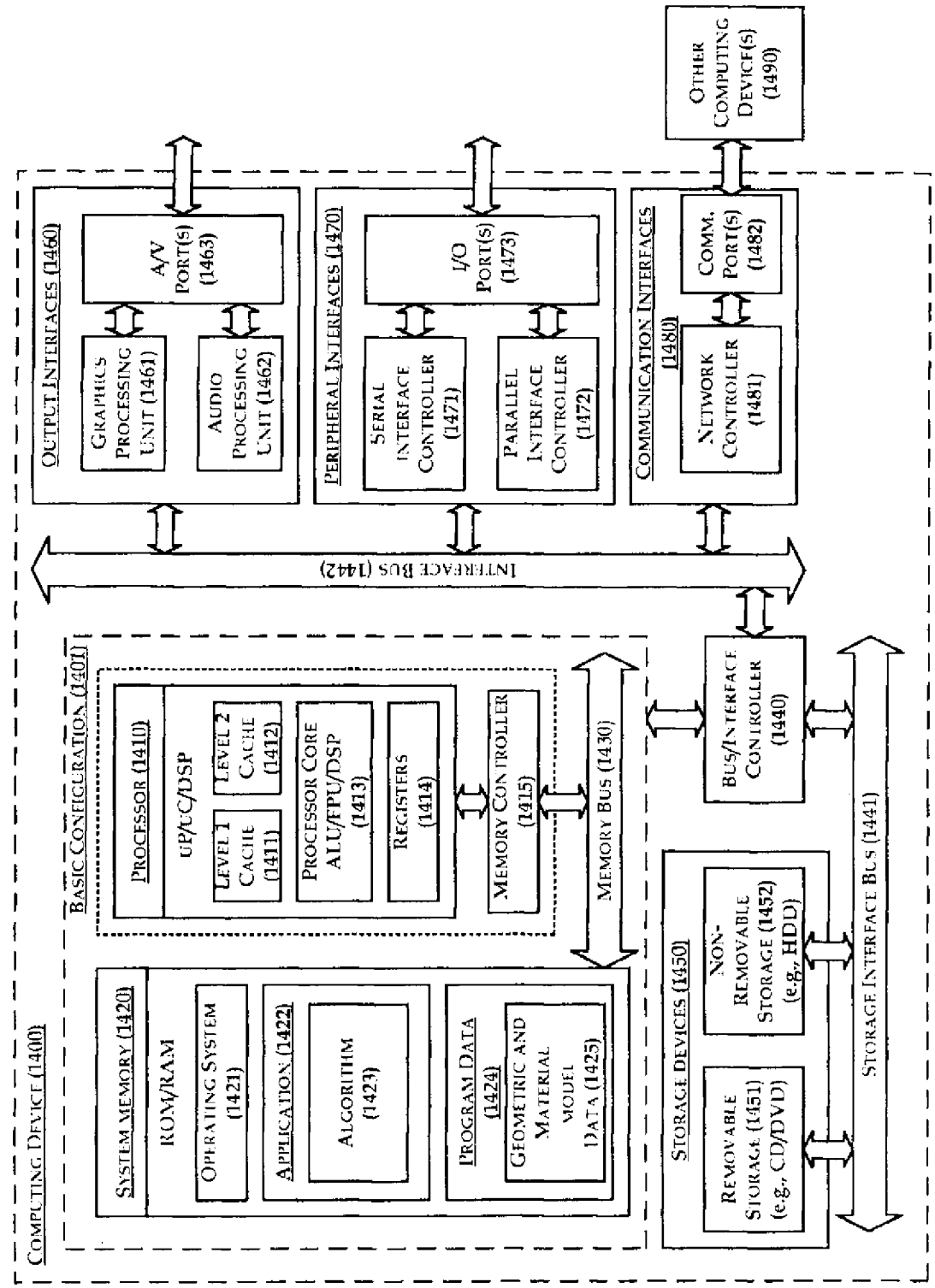

FIG. 14 is a block diagram illustrating an example computing device 1400 arranged for generating a raster tool path, as described herein. In a very basic configuration 1401, computing device 1400 typically includes one or more processors 1410 and system memory 1420. A memory bus 1430 can be used for communicating between the processor 1410 and the system memory 1420.

Depending on the desired configuration, processor 1410 can be of any type including but not limited to a microprocessor (µP), a microcontroller (µC), a digital signal processor (DSP), or any combination thereof. Processor 1410 can include one more levels of caching, such as a level one cache 1411 and a level two cache 1412, a processor core 1413, and registers 1414. The processor core 1413 can include an arithmetic logic unit (ALU), a floating point unit (FPU), a digital signal processing core (DSP Core), or any combination thereof. A memory controller 1415 can also be used with the processor 1410, or in some implementations the memory controller 1415 can be an internal part of the processor 1410.

Depending on the desired configuration, the system memory 1420 can be of any type including but not limited to volatile memory (such as RAM), non-volatile memory (such as ROM, flash memory, etc.) or any combination thereof. System memory 1420 typically includes an operating system 1421, one or more applications 1422, and program data 1424. Application 1422 includes geometric and material modeling, and fractal curve selection algorithms 1423 that may be arranged to create the fractal curve representation of the object. Program Data 1424 includes geometric and material model data 1425. In some example embodiments, application 1422 can be arranged to operate with program data 1424 on an operating system 1421. This described basic configuration is illustrated in FIG. 14 by those components within dashed line 1401.

Computing device 1400 can have additional features or functionality, and additional interfaces to facilitate communications between the basic configuration 1401 and any required devices and interfaces. For example, a bus/interface controller 1440 can be used to facilitate communications between the basic configuration 1401 and one or more data storage devices 1450 via a storage interface bus 1441. The data storage devices 1450 can be removable storage devices 1451, non-removable storage devices 1452, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media can include volatile and nonvolatile, removable and non-removable media implemented in any method or technology for storage of information, such as computer readable instructions, data structures, program modules, or other data.

System memory 1420, removable storage 1451 and non-removable storage 1452 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 1400. Any such computer storage media can be part of device 1400.

Computing device 1400 can also include an interface bus 1442 for facilitating communication from various interface devices (e.g., output interfaces, peripheral interfaces, and communication interfaces) to the basic configuration 1401 via the bus/interface controller 1440. Example output interfaces 1460 include a graphics processing unit 1461 and an audio processing unit 1462, which can be configured to communicate to various external devices such as a display or speakers via one or more A/V ports 1463. Example peripheral interfaces 1460 include a serial interface controller 1471 or a parallel interface controller 1472, which can be configured to communicate with external devices such as input devices (e.g., keyboard, mouse, pen, voice input device, touch input device, etc.) or other peripheral devices (e.g., printer, scanner, etc.) via one or more I/O ports 1473. An example communication interface 1480 includes a network controller 1481, which can be arranged to facilitate communications with one or more other computing devices 1490 over a network communication via one or more communication ports 1482. The communication connection is one example of a communication media. Communication media may typically be embodied by computer readable instructions, data structures, program modules, or other data in a modulated data signal, such as a carrier wave or other transport mechanism, and includes any information delivery media. A "modulated data signal" can be a signal that has one or more of its characteristics set or changed in such a manner as to encode information in the signal. By way of example, and not limitation, communication media can include wired media such as a wired network or direct-wired connection, and wireless media such as acoustic, radio frequency (RF), infrared (IR) and other wireless media. The term computer readable media as used herein can include both storage media and communication media.

Computing device 1400 can be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 1200 can also be implemented as a personal computer including both laptop computer and non-laptop computer configurations.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or, "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for modeling an object, the method comprising:
   determining, by a computing device, a resolution of a portion of the object based on a material porosity model that represents the object;
   determining, by the computing device, a material porosity contour for a portion of the material porosity model;
   determining, by the computing device, a fractal space filling curve type and a level of decomposition based on the resolution of the portion of the object; and
   generating, by the computing device, a fractal curve representation of the portion of the object based on the material porosity contour and using the determined fractal space filling curve type and level of decomposition.

2. The method of claim 1, further comprising:
   determining a second fractal space filling curve type and level of decomposition for a second portion of the object;
   generating a second fractal curve representation of the second portion of the object using the determined second fractal space filling curve type and level of decomposition; and
   combining the fractal curve representation and the second fractal curve representation to create a continuous fractal curve representation of the object.

3. The method of claim 2, further comprising:
   receiving data representative of a boundary of the object; and
   modifying the continuous fractal curve representation of the object based on the data representative of the boundary of the object.

4. The method of claim 3, wherein modifying the continuous fractal curve representation of the object based on the data representative of the boundary of the object comprises:
   determining one or more points of intersection of the continuous fractal curve representation with the data representative of the boundary of the object; and
   modifying the continuous fractal curve representation at the one or more points of intersection.

5. The method of claim 1, further comprising defining instructions executable by a manufacturing tool to create a model of the object according to the fractal curve representation of the portion of the object.

6. The method of claim 5, further comprising:
receiving data representative of a boundary of the object;
determining one or more points of intersection of the fractal curve representation with the data representative of the boundary of the object; and
modifying the fractal curve representation at the one or more points of intersection.

7. The method of claim 6, wherein defining instructions executable by the manufacturing tool to create the model of the object according to the fractal curve representation of the portion of the object comprises:
defining instructions indicating for the manufacturing tool to be off while the manufacturing tool traverses between two points of intersection of the fractal curve representation with the data representative of the boundary of the object.

8. The method of claim 1, wherein generating the fractal curve representation of the portion of the object comprises generating the fractal curve representation of a layer of the object, and wherein the method further comprises generating a respective fractal curve representation of each layer of the object.

9. The method of claim 1, further comprising:
determining, based on the material porosity model, a combination of fractal space filling curve types for respective portions of the object;
generating respective fractal curve representations of the respective portions of the object using the determined respective fractal space filling curve types; and
combining the respective fractal curve representations.

10. The method of claim 1, further comprising:
receiving a model of the object, wherein the model includes a geometrical model and the material porosity model; and
dividing the material porosity model into a series of two-dimensional layer representations, wherein each two-dimensional layer represents a cross-section of the material porosity model of the object and is indicative of a material porosity variation for the two-dimensional layer representative of the resolution of the portion of the object.

11. The method of claim 1, wherein an area fraction A in a unit square filled by the fractal space filling curve type in the fractal curve representation is given by $A=N*d*w$, where N is a number of line segments, d is a length of a line segment, and w is a road width of a given tool used to create the object in physical space, and wherein the area fraction A of all unit squares corresponds to a porosity of the object.

12. The method of claim 11, wherein determining the fractal space filling curve type and the level of decomposition comprises selecting a fractal curve and level of decomposition of the fractal curve for a fixed road width w of a given tool based on the area fraction A and a thickness of a layer of the object to obtain the material porosity contour.

13. The method of claim 1, further comprising using the fractal curve representation to create a cross section of the object in physical space using a solid free form technique selected from the group consisting of 3D printing, fused deposition, stereolithography, selective laser sintering, and direct material deposition.

14. The method of claim 1, wherein generating the fractal curve representation comprises using space-filling fractal curves selected from the group consisting of Peano curves, Hilbert curves, E-curve curves, Macrotile 3×3 curves, and Macrotile 4×4 curves.

15. A non-transitory computer readable medium having stored therein instructions executable by a computing device to cause the computing device to perform operations comprising:
determining, a resolution of a portion of an object based on a material porosity model that represents the object;
determining a material porosity contour for a portion of the material porosity model;
determining a fractal space filling curve type and a level of decomposition based on the resolution of the portion of the object; and
generating a fractal curve representation of the portion of the object based on the material porosity contour and using the determined fractal space filling curve type and level of decomposition.

16. The non-transitory computer readable medium of claim 15, wherein the operations further comprise:
determining a second fractal space filling curve type and level of decomposition for a second portion of the object;
generating a second fractal curve representation of the second portion of the object using the determined second fractal space filling curve type and level of decomposition; and
combining the fractal curve representation and the second fractal curve representation to create a continuous fractal curve representation of the object.

17. The non-transitory computer readable medium of claim 15, wherein the generating the fractal curve representation of the portion of the object comprises generating the fractal curve representation of a layer of the object, and wherein the operations further comprise generating a respective fractal curve representation of each layer of the object.

18. The non-transitory computer readable medium of claim 15, wherein the operations further comprise:
determining, based on the material porosity model, a combination of fractal space filling curve types for respective portions of the object;
generating respective fractal curve representations of the respective portions of the object using the determined respective fractal space filling curve types; and
combining the respective fractal curve representations.

19. A system comprising:
a processor; and
machine language instructions stored on a data storage medium and executable by the processor to perform operations comprising:
determining, a resolution of a portion of an object based on a material porosity model that represents the object;
determining a material porosity contour for a portion of the material porosity model;
determining a fractal space filling curve type and a level of decomposition based on the resolution of the portion of the object; and
generating a fractal curve representation of the portion of the object based on the material porosity contour and using the determined fractal space filling curve type and level of decomposition.

20. The system of claim 19, wherein the operations further comprise:
determining a second fractal space filling curve type and level of decomposition for a second portion of the object;

generating a second fractal curve representation of the second portion of the object using the determined second fractal space filling curve type and level of decomposition; and combining the fractal curve representation and the second fractal curve representation to create a continuous fractal curve representation of the object.

\* \* \* \* \*

UNITED STATES PATENT AND TRADEMARK OFFICE
CERTIFICATE OF CORRECTION

PATENT NO. : 8,660,825 B2
APPLICATION NO. : 13/564547
DATED : February 25, 2014
INVENTOR(S) : Kumar It is certified that error appears in the above-identified patent and that said Letters Patent is hereby corrected as shown below:

On Title Page 2, References Cited, item (56), under "OTHER PUBLICATIONS", in Column 1, Line 2, delete "computeraided" and insert -- computer aided --, therefor.

In the Drawings

In Fig. 14, Sheet 18 of 18, replace the figure with the attached Replacement Sheet.

In the Specification

In Column 1, Line 29, delete "congential anomalies," and insert -- congenital anomalies, --, therefor.

In Column 4, Line 39, delete "ink jet" and insert -- ink-jet --, therefor.

In Column 4, Line 55, delete "Materilise" and insert -- Materialise --, therefor.

In Column 6, Line 3, delete "($GC_i$=1, 2…n))" and insert -- ($GC_i$, i=1, 2…n)) --, therefor.

In Column 6, Line 8, delete "($GC_i$=1, 2…n)" and insert -- ($GC_i$, i=1, 2…n) --, therefor.

In Column 8, Line 12, delete "iso Z" and insert -- iso-Z --, therefor.

In Column 12, Line 43, delete "(MC)" and insert -- (MCi) --, therefor.

In Column 16, Line 10, delete "interfaces 1460" and insert -- interfaces 1470 --, therefor.

In Column 16, Line 41, delete "device 1200" and insert -- device 1400 --, therefor.

In Column 17, Lines 56-57, delete ""A" or, "B"" and insert -- "A" or "B" --, therefor.

Signed and Sealed this
Twenty-ninth Day of July, 2014

Michelle K. Lee
*Deputy Director of the United States Patent and Trademark Office*